United States Patent [19]

Emmick

[11] 3,962,282
[45] June 8, 1976

[54] JUVENILE HORMONE MIMICS

[75] Inventor: Thomas L. Emmick, Greenfield, Ind.

[73] Assignee: Eli Lilly and Company, Indianapolis, Ind.

[22] Filed: July 3, 1974

[21] Appl. No.: 485,486

Related U.S. Application Data

[60] Division of Ser. No. 187,890, Oct. 8, 1971, Pat. No. 3,825,661, which is a continuation-in-part of Ser. No. 877,019, Nov. 14, 1969, abandoned, which is a continuation-in-part of Ser. No. 787,281, Dec. 26, 1968, abandoned.

[52] U.S. Cl. .......................... 260/340.5; 260/240 R; 260/327 M; 260/329 R; 260/476 R; 260/577; 260/645
[51] Int. Cl.² .............. C07D 317/50; C07D 319/08
[58] Field of Search ............................ 260/340.5

[56] References Cited
UNITED STATES PATENTS

| | | | |
|---|---|---|---|
| 3,563,982 | 2/1971 | Bowers | 260/340.5 |
| 3,637,752 | 1/1972 | Siddall | 260/340.5 |
| 3,766,209 | 10/1973 | Emmick | 260/340.5 |
| 3,787,443 | 1/1974 | Erickson | 260/340.5 |
| 3,829,577 | 8/1974 | Chodnekav | 260/340.5 |

OTHER PUBLICATIONS

Weygand, "Preparative Organic Chemistry," (1972), pp. 105, 106, 122, 123 & 124.

*Primary Examiner*—Lorraine A. Weinberger
*Assistant Examiner*—Michael Shippen
*Attorney, Agent, or Firm*—Leroy Whitaker; Everet F. Smith

[57] ABSTRACT

Insect populations are controlled by treating an immature form of the insect with a novel compound possessing juvenile hormone-like activity. Such a compound is one having the formula

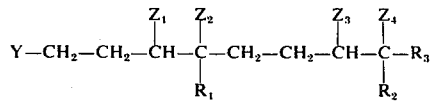

wherein Y is thienyl, phenyl or substituted phenyl. For example, 9-(3,4-methylenedioxyphenyl)-2,6-dimethyl-2,6-nonadiene exhibits very good activity.

3 Claims, No Drawings

JUVENILE HORMONE MIMICS

CROSS-REFERENCE

This application is a division of my copending application Ser. No. 187,890, filed Oct. 8, 1971, now U.S. Pat. No. 3,825,661, which in turn is a continuation-in-part of my then copending application Ser. No. 877,019, filed Nov. 14, 1969, now abandoned, which in turn is a continuation-in-part of then copending application Ser. No. 787,281, filed Dec. 26, 1968, now abandoned.

BACKGROUND OF THE INVENTION

This invention concerns a series of compounds which exhibit juvenile hormone-like activity. More particularly, this invention is concerned with a series of compounds comprising a long carbon chain containing at least 11 carbon atoms to which is attached a thiophene, benzene or substituted benzene ring.

It is well known to control insects by treating a metamorphic stage of the insect with a juvenile hormone to prevent passage of the insect to a subsequent metamorphic stage. As a result of such treatment the insect will not achieve full maturity. The structure of two such hormones, Juvenile Hormones I and II, are shown below.

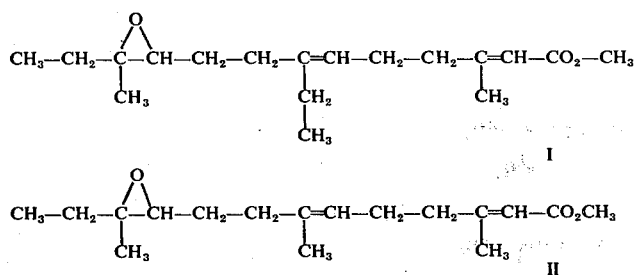

I

II

A series of synthetically prepared compounds having juvenile hormone-like activity are described in South African Pat. No. 67/5149. These compounds, like the naturally occurring hormones, have a straight-chain carbon skeleton. This carbon skeleton is terminated by such groups as ester, hydroxy, halo, and amino.

Wigglesworth, J. Ins. Physiol. 9, 105 (1963), reported that dendrolasin exhibits some juvenile hormone activity. Dendrolasin is a naturally-occurring compound secreted by the mandibular gland of the ant. Chemically, it is 9-(2-furyl)-2,6-dimethyl-2,6-nonadiene.

In the course of synthetic studies in the diterpene series Nasipuri et al., J. Chem Soc., 1964, 2146, prepared 9-(3-methoxyphenyl)-2,6-dimethyl-2,6-nonadiene by means of the Wittig reaction. There was no suggestion that the compound possesses biological activity.

SUMMARY

I have now discovered a class of compounds having juvenile hormone-like activity. My compounds comprise a hydrocarbon chain of at least 11 carbon atoms to which is attached a thiophene, benzene or substituted benzene ring. The development of specific species of insect populations are controlled by treating immature forms of specific species of insects with a maturation-inhibiting amount of one of my compounds. The compounds are effective when ingested by the immature insect form or when the immature insect form is contacted with the compound.

DESCRIPTION OF THE PREFERRED EMBODIMENT

The compounds of my invention are those having the following formula

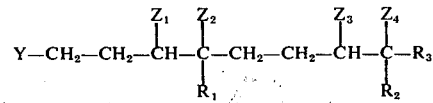

wherein
each of $R_1$, $R_2$ and $R_3$ is a $C_1$–$C_3$ alkyl group;
each of $Z_1$, $Z_2$, $Z_3$, and $Z_4$ separately is hydrogen or halogen, or $Z_1$ and $Z_2$ together or $Z_3$ and $Z_4$ together are oxygen or a carbon to carbon bond; and
Y is thienyl, phenyl or substituted phenyl wherein the substituents are fluoro, chloro, bromo, carboethoxy, cyano, methoxy, ethoxy, methylenedioxy, ethylenedioxy, $C_1$–$C_4$ alkyl, nitro, dimethylamino or diethylamino.

Thus, for example, each of $R_1$, $R_2$, and $R_3$ may be such groups as methyl, ethyl, n-propyl, and isopropyl. It is to be understood that all R groups need not be the same in a particular molecule but that each R can take on a value independent of the others.

It is to be understood that $Z_1$ and $Z_2$ are related as are $Z_3$ and $Z_4$. Taken separately, each Z may be hydrogen or halogen. $Z_1$ and $Z_2$ taken together may be an oxygen atom to form an epoxy group or a carbon to carbon bond so that there is a double bond between the carbon atoms to which $Z_1$ and $Z_2$ are attached. $Z_3$ and $Z_4$ may also be taken separately or together in this same manner. Halogens that may be employed include chlorine, bromine, fluorine, or iodine. Chlorine is preferred.

Y represents thienyl phenyl or substituted phenyl such as 4-cyanophenyl, 4-dimethylaminophenyl, 3-bromophenyl, 3,4-dichlorophenyl, 2,6-dichlorophenyl, 3-methylphenyl, 4-fluorophenyl, 3,4-methylenedioxyphenyl, 2,4-diethoxyphenyl, 2,3-dimethoxyphenyl, 4-carboethoxyphenyl, 4-ethylphenyl, 4-isopropylphenyl, or 3-nitrophenyl.

The preferred compounds of my invention are those in which $R_1$, $R_2$, and $R_3$ are methyl or ethyl, each Z separately is hydrogen or $Z_1$ and $Z_2$ together and $Z_3$ and $Z_4$ together are oxygen or carbon to carbon bonds, and Y is m-methoxyphenyl, p-methoxyphenyl, 3,4-dimethoxyphenyl, 4-chlorophenyl, 3,4-methylenedioxyphenyl, or 3,4-ethylenedioxyphenyl. The trans isomers of the unsaturated compounds are preferred over the cis isomers. Particularly preferred are those compounds having the following structures.
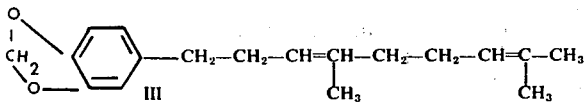
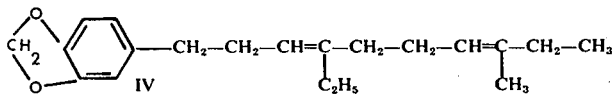
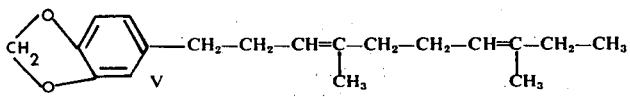
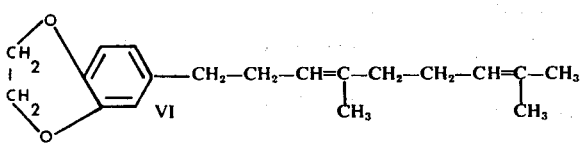
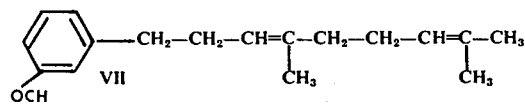
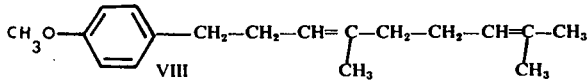
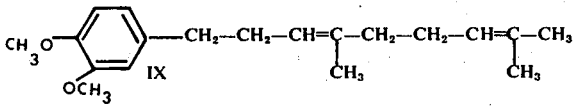
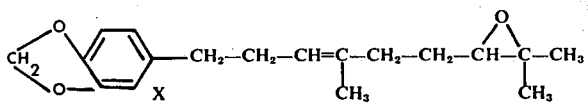
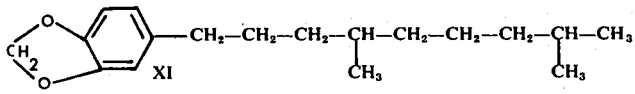
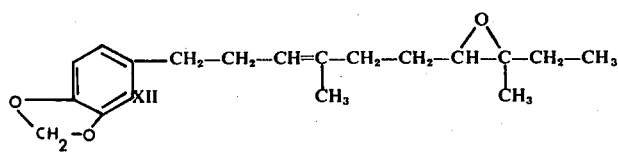
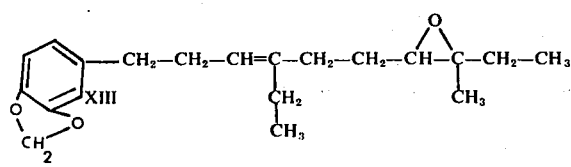

-continued

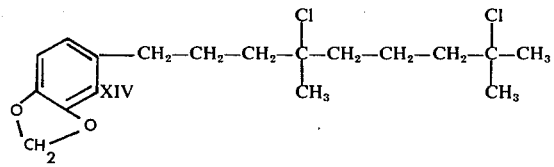

Some of the compounds of my invention may be prepared by a five-step synthesis starting with the proper cinnamic acid. Where practical, the cinnamic acid for use in my process is one substituted in the benzene ring with those substituents which are desired in the final product. It will be apparent to a skilled chemist that it will sometimes be necessary to introduce substituents onto the ring at some intermediate point in my synthesis. Such a procedure does not detract from my overall synthesis. By means of my process the cinnamic acid side chain is expanded to the side chain found in the product.

As the first step of my process it is necessary to hydrogenate the double bond in the cinnamic acid side chain. The hydrogenation of carbon-carbon double bonds is well known to those skilled in the art and may be accomplished in the presence of the proper hydrogenation catalyst. I have found a catalyst of palladium on carbon to work quite well in this hydrogenation step. The reaction may be conducted at a temperature within the range of 0° to 100°C. and preferably within the range of 20°–40°C. at a pressure of up to 100 psig. and preferably at 30–50 psig. This pressure is the initial pressure in the reaction vessel and will decrease as hydrogen is consumed unless additional hydrogen is added to the vessel. The addition of more hydrogen is not essential to the process.

In the second step of my process the carboxyl group of the phenylpropionic acid obtained by hydrogenation of the cinnamic acid is reduced to a hydroxymethyl group. Means for reducing a carboxyl group are also known to those skilled in the art. I prefer to use lithium aluminum hydride as the reducing agent in an inert solvent such as diethyl ether. The acid may be added as a solid to a solution of the lithium aluminum hydride in the solvent. However, I have obtained better results when the acid is added continuously in solution in the solvent. The temperature is preferably kept below 50°C. and still more preferably below about 35°C. When ether is employed as the solvent the reaction proceeds readily at the reflux temperature.

The phenylpropanol obtained in the preceding step is next treated with a phosphorus trihalide to replace the hydroxyl group with halogen. This reaction proceeds readily upon the addition of the phosphorous trihalide to a solution of the alcohol in an inert solvent such as carbon tetrachloride. The reaction is a mildly exothermic one and the temperature may be allowed to rise during the addition period. At the completion of the addition of the phosphorus trihalide the reaction mixture is preferably heated at a temperature of 50° to 100°C. for a brief time of from say 5 to 30 minutes to insure complete reaction. I prefer to use phosphorous tribromide in this step.

Reaction of the halide from Step 3 with triphenylphosphine results in the preparation of a phosphonium halide. This reaction is preferably conducted in an inert hydrocarbon solvent such as benzene, toluene, or xylene. The temperature to be employed depends upon the substituents present in the benzene ring of the propyl halide. Stability problems arise with certain members of the series if temperatures much above 80°C. are used. The reaction does proceed at temperatures of around 80°C. and no stability problems are encountered at this temperature. With stable materials reaction temperatures in excess of 80°C. may be employed to increase the reaction rate.

The phosphonium halides obtained at this step in the process are key intermediates for the preparation of the final active products. These phosphonium halides are represented by the formula

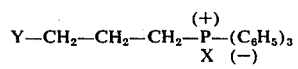

wherein Y has the values assigned above and X is halogen such as bromine or chlorine. Of particular interest are those phosphonium bromides wherein Y is m-methoxyphenyl, p-methoxyphenyl, 3,4-methylenedioxyphenyl, or 3,4-ethylenedioxyphenyl.

In the final step of the process the phosphonium halide from step 4 is reacted with the appropriate ketone in the presence of a base in the well-known Wittig reaction. This reaction is preferably conducted in a solvent under nitrogen at a temperature of 0° to 50°C. and preferably 10° to 30°C. Bases that have been typically employed in the Wittig reaction include sodium hydride, sodium amide, and butyllithium in such solvents as dimethyl sulfoxide and benzene. I have obtained good results in my process with butyllithium in dimethyl sulfoxide.

The ketone for use in this step of my process is one having the structure

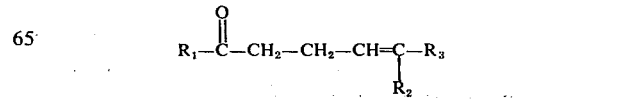

wherein $R_1$, $R_2$, and $R_3$ have the values assigned above. Any known method may be used in preparing these ketones. One such method is described, for example, in South African Pat. No. 67/5149.

This method of preparing the compounds of my invention will be further illustrated by the following examples. It is to be understood that these examples are merely illustrative and are not intended to limit the scope of the invention in any manner.

EXAMPLE 1

To a solution of 50 g. of 3,4-methylenedioxycinnamic acid in 200 ml. of a 2 N potassium carbonate solution in a Parr shaker was added 0.5 g. of a five percent palladium on carbon catalyst. Hydrogen was introduced into the reactor to a pressure of 30 psig. The reaction was allowed to proceed until 0.26 moles of hydrogen were taken up (about 4 hours). At the completion of the reaction the mixture was filtered to remove the catalyst. Acidification of the mixture resulted in the precipitation of the desired 3,4-methylenedioxyphenylpropionic acid in 95 percent yield.

EXAMPLE 2

To a suspension of 13.2 g. of lithium aluminum hydride in 500 ml. of anhydrous ether was added 45 g. of 3-(3,4-methylenedioxyphenyl)propionic acid, prepared as in Example 1, in small portions as a solid at room temperature with rapid stirring. Following addition, the reaction mixture was heated under reflux overnight. The reaction mixture was cooled to 0° to 10°C. and 13.2 ml. of water, 13.2 ml. of 15 percent sodium hydroxide solution, and 39.6 ml. of water were added in that order. After stirring at room temperature for 1 hour the mixture was filtered to remove salts and the ether fraction was separated and dried over magnesium sulfate. Evaporation of the ether at reduced pressure yielded 41.5 g. of crude 3-(3,4-methylenedioxyphenyl)propyl alcohol which was used in subsequent reactions without further purification.

I have obtained better results in the reduction of the carboxyl group when the acid is added to the suspension of lithium aluminum hydride as a solution over a period of time. I therefore recommend that the acid be added as a solution rather than as a solid.

EXAMPLE 3

To a solution of 41.2 g. of 3-(3,4-methylenedioxyphenyl)propyl alcohol in 66 ml. of carbon tetrachloride was added dropwise with stirring 34 g. of phosphorous tribromide over a 20-minute period. The reaction temperature rose to 45°C. during this addition. The reaction mixture was then heated at 70°C. for 10 minutes and poured onto 200 ml. of crushed ice. This heterogeneous mixture was separated and the aqueous portion was extracted with 400 ml. of carbon tetrachloride. The extract was combined with the organic layer from the reaction mixture and the combined fractions washed with saturated sodium bicarbonate solution and saturated sodium chloride solution in that order and dried over magnesium sulfate. After 1 hour the solution was filtered, the carbon tetrachloride was removed under reduced pressure and the residue was distilled at 0.5 mm. of mercury at an overhead temperature of 116° to 119°C. to give 32 g. of the desired 3-(3,4-methylenedioxyphenyl)propyl bromide.

EXAMPLE 4

A solution of 40 g. of 3-(p-methoxyphenyl)propyl bromide and 49.3 g. of triphenylphosphine in 500 ml. of benzene was heated under reflux under nitrogen for 96 hours. The solid which precipitated was removed by filtration. This solid weighed 40 g. The benzene was removed from the solution under reduced pressure and 250 ml. of o-xylene was added to the residue. This solution was heated under reflux an additional 3 days. The solid resulting from this reaction was recrystallized from benzene-hexane to yield an additional 35 g. of product. The 3-(p-methoxyphenyl)propyltriphenylphosphonium bromide product had a melting point of 158° to 161°C.

Analysis: Calculated for $C_{28}H_{28}BrOP$: C, 68.25; H, 5.72; Br, 15.62. Found: C, 67.96; H, 5.76; Br, 15.45.

Following the procedure of Example 4 the following additional phosphonium bromides were also prepared.

| Compound | Melting Point, °C. |
| --- | --- |
| 3-(m-methoxyphenyl)propyltriphenylphosphonium bromide | 126–129 |
| 3-(3,4-methylenedioxyphenyl)propyl triphenylphosphonium bromide | 188–190 |

EXAMPLE 5

A solution of 0.071 mole of butyllithium in 32.2 ml. of hexane was added to 50 ml. of anhydrous dimethyl sulfoxide. Following the evolution of butane 35.0 g. of 3-(p-methoxyphenyl)propyltriphenylphosphonium bromide was added portion-wise over a period of 10 minutes. The resulting deep red solution was stirred for two hours at room temperature under nitrogen. To the mixture was then added a solution of 9.0 g. of 6-methyl-5-heptene-2-one in 10 ml. of dimethyl sulfoxide. Stirring at room temperature was continued for 16 hours following the addition of the ketone. The reaction mixture was diluted with 350 ml. of water and the mixture was extracted twice with ether. The ether solutions were combined, washed with water, washed with saturated aqueous sodium chloride solution, and dried over magnesium sulfate. The ether was removed at reduced pressure and the resulting residue was placed on a column of 1 kg. of silica gel in benzene solution. Elution was carried out with benzene, with fractions of 20 ml. volume being collected. The desired product was initially eluted in fraction 73. Fractions 73 to 150 were combined to give the desired product. The nuclear magnetic resonance spectra confirmed the expected structure as represented by formula VIII.

Analysis: Calculated for $C_{18}H_{28}O$: C, 83.66; H, 10.14. Found: C, 83.90; H, 10.45.

EXAMPLE 6

The procedure of Example 5 was repeated employing the m-methoxyphenyl compound in place of the p-methoxyphenyl compound. The product was evaporatively distilled at 105°C. and 40 microns pressure. The infrared and nuclear magnetic resonance spectra confirmed the product to have the expected structure VII.

Analysis: Calculated for $C_{18}H_{26}O$: C, 83.66; H, 10.14. Found: C, 83.94; H, 10.11.

EXAMPLE 7

The procedure of Example 5 was repeated using the 3,4-dimethoxyphenyl compound in place of the p-methoxyphenyl compound. The product from this reaction was evaporatively distilled at 120°C. and 40 microns pressure. The nuclear magnetic resonance spectra was that expected for the desired product IX.

Analysis: Calculated for $C_{19}H_{28}O_2$: C, 79.12; H, 9.75. Found: C, 79.34; H, 9.54.

EXAMPLE 8

The procedure of Example 5 was repeated employing the 3,4-methylenedioxyphenyl compound in place of the p-methoxyphenyl compound. The product was chromatographed over silica gel and then evaporatively distilled at 100° to 125°C. and 60 to 80 microns pressure. Structure III was confirmed by nuclear magnetic spectroscopy.

Analysis: Calculated for $C_{18}H_{24}O_2$: C, 79.37; H, 8.88. Found: C, 79.14; H, 8.62.

EXAMPLE 9

The procedure of Example 8 was repeated using 3-methyl-3-nonene-7-one as the ketone. The product was purified by chromatography over silica and evaporative distillation at 60 microns pressure and 150°C. The nuclear magnetic resonance spectrum confirmed structure IV.

Analysis: Calculated for $C_{20}H_{28}O_2$: C, 79.79; H, 9.41. Found: C, 79.95; H, 9.39.

EXAMPLE 10

Example 8 was repeated using 3-methyl-3-octene-7-one as the ketone. The product was purified by chromatography over silica gel and evaporatively distilled at 150°C. and 150 microns. Structure V was confirmed by the nuclear magnetic resonance spectrum.

EXAMPLE 11

3-(3,4-Dihydroxyphenyl)propionic acid (50 g.) was added to a cool solution of 55 g. of potassium hydroxide in 200 ml. of water. To this solution was added 56.4 g. of 1,2-dibromoethane and the resulting mixture was heated under reflux with stirring for 90 minutes. The mixture was cooled, chloroform was added, the aqueous portion was acidified with concentrated hydrochloric acid, and the layers were separated. The chloroform solution was washed with water and saturated aqueous sodium chloride solution and dried over magnesium sulfate. After filtering, the bulk of the chloroform was removed at 40°C. under reduced pressure, with the temperature being raised to 50°C. to remove the last trace of chloroform. A nuclear magnetic resonance spectrum confirmed that the desired 3-(3,4-ethylenedioxyphenyl)propionic acid had been obtained in high purity. The yield was 22 g.

EXAMPLE 12

The product from Example 11 was treated with lithium aluminum hydride as described in Example 2. The desired 3-(3,4-ethylenedioxyphenyl)propyl alcohol was obtained in an 18 g. yield.

EXAMPLE 13

The alcohol from Example 12 was treated with phosphorous tribromide as described in Example 3. The yield of the described 3-(3,4-ethylenedioxyphenyl)propyl bromide was 17.1 g. The structure was confirmed by the nuclear magnetic resonance spectrum.

EXAMPLE 14

3-(3,4-Ethylenedioxyphenyl)propyltriphenylphosphonium bromide was prepared by treating the bromide from Example 13 with triphenylphosphine following a procedure similar to that of Example 4 except that the reaction mixture was stirred as a melt with no solvent at 90°C. and 10 mm. pressure. The yield of product melting at 195°–198°C. was 22 g. The structure was confirmed by the nuclear magnetic resonance spectrum.

EXAMPLE 15

The phosphonium bromide from Example 14 was treated as described in Example 5 to yield the desired 9-(3,4-ethylenedioxyphenyl)-2,6-dimethyl-2,6-nonadiene (VI). The structure was confirmed by nuclear magnetic resonance spectroscopy.

EXAMPLE 16

3-Hydroxycinnamic acid was converted to 3-ethoxycinnamic acid in the following manner. A solution of 25 g. of 3-hydroxycinnamic acid, 10 g. of sodium hydroxide and 32 g. of ethyl bromide in 300 ml. of ethanol was heated under reflux for 16 hours. Water was added and the mixture was acidified to precipitate the free acid product which was collected by filtration. Approximately 8 g. was obtained. The alcohol was distilled from the filtrate under reduced pressure. The resulting solution was extracted twice with benzene. The benzene extracts were combined, washed with brine, dried over magnesium sulfate, and the benzene evaporated to yield about 17 g. of the ethyl ester of 3-ethoxycinnamic acid.

The ester was treated as described in Example 1–5 to obtain 9-(3-ethoxyphenyl)-2,6-dimethyl-2,6nonadiene. The structure was confirmed by nuclear magnetic resonance spectroscopy.

EXAMPLE 17

3-(3,5-Dimethoxyphenyl)propionic acid was treated as described in Examples 2–5 to obtain 9-(3,5-dimethoxyphenyl)-2,6-dimethyl-2,6-nonadiene. The product distilled at 120°C. at 60 microns pressure. The structure was confirmed by nuclear magnetic resonance spectroscopy.

It is apparent that a wide scope of compounds of my invention can be prepared using the process I have described by choosing the proper cinnamic acid and ketone starting materials. It is to be understood that the proper substituents may be introduced into the benzene ring after hydrogenation of the cinnamic acid double bond. Such a procedure is equivalent to the introduction of substituents before hydrogenation. The former procedure is illustrated by Example 11.

My compounds can also be prepared by a Grignard coupling of a properly substituted benzyl halide and an aliphatic halide such as geranyl chloride or octyl bromide. The Grignard reaction is a well-known method of coupling two halides together. The Grignard reagent may be prepared from either the benzyl halide or the aliphatic halide and the coupled with the other. The following examples will illustrate this method of preparation.

EXAMPLE 18

A solution of 154.3 g. of geraniol in 1.25 l. of anhydrous tetrahydrofuran was cooled to 0°C. To this solution maintained at 0°C. was added dropwise with stirring a solution of one mole of butyllithium in hexane (about 440 ml.). After all the butyllithium had been added, 84 g. of solid lithium chloride was added in one portion. A solution of 190.5 g. of p-toluenesulfonyl chloride in 750 ml. of anhydrous tetrahydrofuran was then added dropwise at 0°C. The mixture was stirred for one-half hour after addition. Approximately 2 l. of water was added and the layers were separated. The aqueous phase was reextracted with 1 l. of ether and the organic fractions were combined, washed successively with saturated aqueous sodium bicarbonate solution, water and saturated aqueous sodium chloride solution. After drying over magnesium sulfate the solvents were removed, having 180 g. of a yellow liquid. This liquid was distilled to yield 118 g. of geranyl chloride, boiling point 73°–74°C. at 3 mm. pressure. The structure was confirmed by nuclear magnetic resonance spectroscopy.

EXAMPLE 19

Benzyl magnesium chloride was prepared by the dropwise addition, under nitrogen, of a solution of 31.8 g. of benzyl chloride in 200 ml. of anhydrous ethyl ether to 6.1 g. of magnesium. Following the addition, the reaction mixture was heated under reflux for 1 hour and then stored overnight under nitrogen at room temperature. The solution was then added dropwise with stirring at room temperature to a solution of 35 g. of geranyl chloride in 50 ml. of anhydrous ether and 100 ml. of hexamethylphosphoramide. When about two-thirds of the benzyl magnesium chloride had been added, a salt precipitated. An additional 100 ml. of hexamethylphosphoramide was added and the reaction mixture was warmed slightly. Addition was resumed and continued until the yellow reaction mixture turned dark brown. Water, 400 ml., and 300 ml. of ether were added. Following acidification of the aqueous phase with dilute hydrochloric acid, the layers were separated and the aqueous phase was reextracted with ether. The other fractions were combined and washed with saturated aqueous sodium bacarbonate solution, water, and saturated aqueous sodium chloride solution. The solution was dried over magnesium sulfate and the ether removed under reduced pressure, leaving 43 g. of a mobile yellow liquid. Chromatography over silica gel using benzene-hexane for elution followed by evaporative distillation at 90°C. and 20 microns pressure gave quite pure trans-2,6-dimethyl-9phenyl-2,6-nonadiene. The structure was confirmed by nuclear magnetic resonance spectroscopy.

Other compounds prepared by the Girgnard coupling reaction were trans-2,6-dimethyl-9-(3-tolyl)-2,6-nonadiene, trans-2,6-dimethyl-9-(3-chlorophenyl)-2,6-nonadiene, trans-2,6-dimethyl-9-(4-chlorophenyl)-2,6-nonadiene, and trans-2,6-dimethyl-9-(3,4-dichlorophenyl)-2,6-nonadiene.

Still others of the compounds to be used in the method of my invention may be prepared by a method I shall refer to as the "dithiane route." This route is depicted by the following equations:

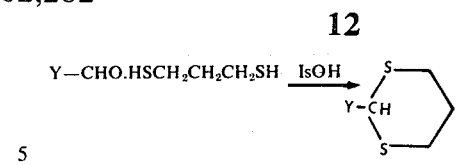

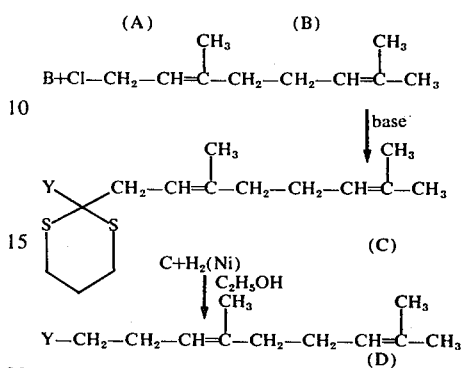

In the first step of the dithiane route an aldehyde is reacted with 1,3-propanedithiol to obtain the 1,3-dithiane. This is a well-known method of blocking carbonyl groups and a skilled chemist would have no difficulty in preparing the dithiane. The reaction is carried out at elevated temperature in the presence of an acidic agent such as p-toluenesulfonic acid. The water of reaction is continuously removed by any convenient means, such as azeotropic distillation. The use of an inert solvent, especially one that forms an azeotrope with water, facilitates the reaction. This step of the process will be illustrated by the following example.

EXAMPLE 20

To a mixture of 30 g. (0.2 mole) of 3,4-methylenedioxybenzaldehyde and 21.8 g. (0.2 mole) of 1,3-propanedithiol in 400 ml. of benzene was added 1.5 g. of p-toluenesulfonic acid. The mixture was heated under reflux for 1 hour with the water formed being collected in a Dean-Stark trap. The reaction mixture was filtered and washed successively with saturated aqueous sodium bicarbonate solution, water, and saturated aqueous sodium chloride solution. After the solution had been dried over magnesium sulfate, the benzene was removed at 40°C. under reduced pressure. The light yellow solid which remained was recrystallized from a benzene-petroleum ether mixture. Recrystallization afforded 38.5 g. of the desired 2-(3,4-methylenedioxyphenyl)-1,3-dithiane, m.p. 95°–96°C.

Analysis: Calculated for $C_{11}H_{12}O_2S_2$: C, 54.97; H, 5.03.

Found: C, 55.15; H, 5.02.

Following the procedure of Example 20 the following dithianes (B) were prepared.

| Y | m.p., °C. |
|---|---|
| (cyclohexyl-like structure with S) | 77–77.5 |
| NC—⟨phenyl⟩— | 107–107.5 |
| $C_2H_5O_2C$—⟨phenyl⟩— | 105–107 |

-continued

| Y | m.p., °C. |
|---|---|
| (CH₃)₂N—C₆H₄— | 121–122 |
| Br—C₆H₄— | 91–92 |
| C₆H₄(Br)— (3-Br) | 86–87 |
| F—C₆H₄— | 104–105 |
| Cl,Cl—C₆H₃— (3,4-di) | 82–83 |

In the second step of the process the dithiane is reacted with a chlorodiene in the presence of a base. This reaction is conducted in an inert solvent in the cold. Temperatures are preferably kept below 0°C., and more preferably below −10°C. Suitable solvents include tetrahydrofuran, dioxane, and the like. The solvent should be thoroughly dried and care should be taken to keep the reaction mixture free of water until the reaction is complete. I have found butyllithium to be a particularly good base for the reaction. At times, it may be desirable to include an amine such as diisopropylamine. This step will be further illustrated by the following examples.

EXAMPLE 21

A solution of 24 g. (0.1 mole) of 2-(3,4-methylenedioxyphenyl)-1,3-dithiane in 200 ml. of THF (dried over CaH₂) was placed under a nitrogen atmosphere and cooled to −30°C. and 50 ml. of a 23 percent solution of n-butyllithium in hexane was added dropwise with stirring. The reaction mixture was stirred for 1.5 hours while maintaining the temperature below −10°C. A solution of 17.3 g. of trans-1-chloro-3,7-dimethyl-2,6-octadiene in 100 ml. of THF (dried over CaH₂) was then added dropwise with stirring. The reaction mixture was maintained at 0°C. for 70 hours. After acidification to a pH of 6 the reaction mixture was poured into 600 ml. of water. The resulting heterogeneous mixture was extracted three times with petroleum ether, the extracts were combined, washed with saturated aqueous sodium bicarbonate solution, water, and brine, and dried over magnesium sulfate. After evaporation of the petroleum ether there was obtained 30 g. of a light yellow oil. Purification was achieved by chromatographing 15 g. of the oil over 500 g. of silica gel using benzene as the eluent. Fourteen grams of the desired trans-2-(3,7-dimethyl-2,6-octadienyl)-2-(3,4-methylenedioxyphenyl)-1,3-dithiane was obtained.

The structure was confirmed by nuclear magnetic resonance spectroscopy.

Other compounds of formula C prepared by the procedure of Example 21 were those in which Y is 2-thienyl, 4-dimethylaminophenyl, 4-fluorophenyl, and 3,4-dichlorophenyl.

EXAMPLE 22

A solution of 4.5 g. (51 mmoles) of diisopropylamine in 100 ml. of THF (distilled from LiAlH₄) was cooled to −30°C. under an atomsphere of nitrogen. To this cold solution was added dropwise with stirring 23 ml. of a 24 percent solution of n-butyllithium in hexane. A solution of 11.0 g. (50 mmoles) of 2-(4-cyanophenyl)-1,3-dithiane in 50 ml. of THF was added dropwise with stirring at −25° to −30°C. The reaction mixture was stirred at −20° to −40°C. for 2 hours. Trans-1-chloro-3,7-dimethyl-2,6-octadiene (8.6 g., 50 mmoles) in 50 ml. THF was added dropwise with stirring at −30°C. After the reaction mixture has been stirred for 1 hour at about −75°C., it was poured into twice its volume of water. The aqueous phase was twice extracted with petroleum ether and the extracts were combined and washed successively with saturated aqueous sodium bicarbonate solution, water and brine. After drying over magnesium sulfate the petroleum ether was evaporated, leaving 16 g. of a light yellow oil. The oil was purified by chromatography over 400 g. of silica gel using benzene as the eluent. Ten grams of the desired trans-2-(4-cyanophenyl)-2-(3,7-dimethyl-2,6-octadienyl)-1,3-dithiane was obtained pure as shown by nmr.

Using the same procedure trans-2-(4-carboethoxyphenyl)-2-(3,7-dimethyl-2,6-octadienyl)-1,3-dithiane was obtained from 2-(4-carboethoxyphenyl)-1,3-dithiane.

EXAMPLE 23 n-Butyllithium, 13 ml. of a 23 percent solution in hexane, was added dropwise with stirring to 13 ml. of dry dimethyl sulfoxide maintained under an atomsphere of nitrogen. The resulting LiCH₂SOCH₃ was added dropwise with stirring to 7.0 g. (25 mmoles) of 2-(3-bromophenyl)-1,3-dithiane in 130 ml. of THF (dried over CaH₂) maintained at −30°C. under nitrogen. Stirring at −30°C. was continued for 2 hours. Trans-1-chloro-3,7-dimethyl-2,6-octadiene (4.3g., 25 mmoles) in 30 ml. of THF was added at −30°C. The mixture was stirred while being allowed to slowly warm to room temperature overnight. The mixture was poured into twice its volume of ice water and extracted with ether. The ether extract was washed with brine and dried over magnesium sulfate. Removal of the ether at 40°C. under vacuum afforded 12 g. of an oil. Five grams of the oil was purified by chromatography over 100 g. of silica gel, eluting with 1:1 benzene-petroleum ether. Three grams of pure trans-2-(3-bromophenyl)-2-(3,7-dimethyl-2,6-octadienyl)-1,3-dithiane was obtained as confirmed by nmr.

The corresponding 4-bromophenyl compound was also prepared by this procedure.

In the third step of the dithiane route the dithiane ring is cleaved by reduction to leave a methylene group. Care must be exercised to cleave the dithiane without reducing the double bonds in the octadiene chain. I have found Raney nickel to be well suited for this reduction. Those skilled in the art will recognize that there are other reducing agents that can perform this selective reduction. The reduction will be illustrated by Example 24.

EXAMPLE 24

A mixture of 5.0 g. (12.4 mmoles) of trans-2-(4-carboethoxyphenyl)-2-(3,7-dimethyl-2,6-octadienyl)-1,3-dithiane and 48 ml. of settled Raney nickel in 500 ml. of anhydrous ethanol was stirred at room temperature for 3 hours. The Raney nickel was removed by filtration and washed extensively with anhydrous ethanol. The alcohol was removed at 50°C. under vacuum, the residue dissolved in petroleum ether, and the petroleum ether solution washed successively with water and brine. After drying over magnesium sulfate, the petroleum ether was removed at 40°C. under vacuum, leaving 3.4 g. of a colorless oil. The oil was purified by chromatography over 70 g. of silica gel, eluting with 1:1 benzene-petroleum ether. Three grams of spectroscopically (nmr) and gas chromatographically pure ethyl trans-4-(4,8-dimethyl-3,7-nonadienyl)benzoate was obtained.

Other compounds of formula D prepared in this manner were those in which Y is 2-thienyl, 4-cyanophenyl, 4-dimethylaminophenyl, 4-bromophenyl, 3-bromophenyl, 4-fluorophenyl, 3,4-dichlorophenyl and 3,4-methylenedioxyphenyl.

Those compounds wherein one or more of the Z groups is halogen may be obtained by the known procedure of adding a hydrogen halide to one or both of the double bonds in the side chain. This results in one Z of a pair being halogen, while the other is hydrogen. This procedure is illustrated by Example 25.

EXAMPLE 25

Hydrogen chloride was bubbled into 200 ml. of carbon tetrachloride at 0°C. To this solution was added 2.0 g. of 2,6-dimethyl-9-(3,4-methylenedioxyphenyl)-2,6-nonadiene and the mixture was placed in a refrigerator at 0°C. for several hours. Evaporation of the solvent under reduced pressure left 2.5 g. of a viscous oil. The nuclear magnetic resonance spectrum of the product showed only a trace of vinyl absorption indicating that the reaction had proceeded to virtual completion.

The epoxides of my invention can be prepared in the usual manner by the oxidation of the double bond with hydrogen peroxide or a per acid. However, I prefer to prepare the epoxides by way of the halohydrin. The epoxide is obtained from the halohydrin by dehydrohalogenation using a mild base. This process will be further illustrated by the following examples.

EXAMPLE 26

A solution of 5.0 g. of 9-(3,4-methylenedioxyphenyl)-2,6-dimethyl-2,6-nonadiene (prepared as in Example 8) in 73 ml. of dimethoxyethane was prepared. To this solution was added 22 ml. of water and the resulting heterogeneous mixture was cooled to 0°C. To the cooled mixture was added 3.6 g. of N-bromosuccinimide portionwise over a period of 15 minutes. This reaction mixture was stirred overnight at room temperature in the dark. The dimethoxyethane was removed under reduced pressure at 40°C. Ether was added to the resulting mixture and the layers were separated. The aqueous phase was reextracted with ether and the ether solutions were combined and washed with water and saturated aqueous sodium chloride solution. After drying over magnesium sulfate the ether was removed at reduced pressure leaving approximately 6 g. of crude material. This crude product was placed on a column of 150 g. of florisil in a 1:1 benzene-hexane solvent. Elution was begun with 1:1 benzene-hexane and a gradient to 100 percent benzene was begun immediately. The volume of each fraction collected was 20 ml. Fractions 31 to 250 were combined to give approximately 5 g. of product. This product was placed on a column of 120 g. of florisil in hexane and elution with hexane was begun. None of the bromohydrin was eluted in the initial 120 fractions and a gradient to 1:1 benzene-hexane was begun. Fractions 221 to 460 were combined to give 4.5 g. of product. The nuclear magnetic resonance spectrum of this product indicated it to be a mixture with the desired bromohydrin and the epoxide being the major components. This mixture was subjected to dehydrohalogenation without further purification.

EXAMPLE 27

The 4.5 g. of the mixture from Example 26 and 2.8 g. of anhydrous potassium carbonate were combined in 35 ml. of anhydrous methanol and the mixture was stirred at room temperature for 1 hour. The excess potassium carbonate was removed by filtration and the methanol was removed from the filtrate at reduced pressure. Water and ether were added to the residue, the layers were separated and the ether phase was washed with water and saturated aqueous sodium chloride solution. After drying over magnesium sulfate, the ether was removed at 40°C. under reduced pressure. The crude product was chromatographed on 80 g. of deactivated silica using benzene for elution. Fractions 14 through 40 were combined to give 2 g. of the epoxide. The product was evaporatively distilled at 150°C. and was consistent with the structure for the expected 9-(3,4-methylenedioxyphenyl)-2,6-dimethyl-2,3-epoxy-6-nonene (X).

Analysis: Calculated for $C_{18}H_{24}O_3$: C, 74.97; H, 8.39. Found: C, 74.23; H, 8.70.

Those compounds of my invention containing side chain unsaturation may be hydrogenated to reduce the side chain double bonds. That is, those compounds wherein $Z_1$ and $Z_2$ together and $Z_3$ and $Z_4$ together form a carbon to carbon bond may be hydrogenated to obtain those compounds wherein either 2 or 4 of the Z groups are hydrogen. This hydrogenation step is the hydrogenation of a carbon to carbon double bond as discussed in Step 1 of my process for preparing the unsaturated compounds of the invention from a cinnamic acid. Methods of hydrogenating double bonds are well known to those skilled in the art. I have found this hydrogenation to proceed readily employing a catalyst of 5 percent palladium on carbon in an inert hydrocarbon solvent. Equivalent hydrogenation procedures will be apparent to those skilled in the art. The hydrogenation of an unsaturated compound of my invention to obtain a fully saturated compound of my invention will be illustrated by the following example.

EXAMPLE 28

To a solution of 1 g. of 9-(3,4-methylenedioxyphenyl)-2,6-dimethyl-2,6-nonadiene (prepared as in Example 8) in 40 ml. of benzene was added 2.0 g. of a 5 percent palladium on carbon catalyst. Hydrogen was introduced into the reaction vessel to a pressure of 50 psig. This mixture was shaken at room temperature for 16 hours. The catalyst was removed by filtration and the benzene was evaporated under reduced pressure to yield pure 9-(3,4-methylenedioxyphenyl)-2,6-dimethylnonane (XI). The structure was confirmed by nuclear magnetic resonance spectroscopy.

In a first demonstration of the ability of my compounds to inhibit the maturation of insects the compounds were applied topically to a metamorphic stage of four insect species. The compounds were applied in acetone solution at concentrations of 10 percent, 1 percent and 0.5 percent. One microliter of the acetone solution was applied to each test specimen. Ten test specimens were employed for each insect at each concentration and compared to ten acetone controls and ten zero controls. Approximately eight to ten days were required before results could be ascertained.

The insect species used in the test were *Tenebrio molitor pupae;* milkweed bug, fourth nymphal stage; wax moth, fifth larval stage; and Mexican bean beetle, fourth larval stage. At the completion of the test, each specimen was examined for the degree of juvenile and adult characteristics. The milkweed bug, wax moth, and Mexican bean beetle were assigned a numerical rating of 0 to 3 with 0 indicating no effect and 3 indicating the maximum effect or least adult development. Because of differences in morphology the Tenebrio rating scale was 0 to 4. In all cases a rating of 2 or higher means that the insect is incapable of reproduction. The number of specimens in each rating classification are given. The results for the compounds tested are summarized in the following tables. In any test were the total of specimens reported is less than 10, those unreported died in some metamorphic stage. Such deaths indicate control, since the dead insects are not capable of reproducing.

2,6-DIMETHYL-9-(3,4-METHYLENEDIOXYPHENYL)-2,6-NONADIENE

| Insect | Conc.,% | 0 | 1 | 2 | 3 | 4 |
|---|---|---|---|---|---|---|
| Tenebrio | 10 | — | — | — | — | 10 |
|  | 1 | — | — | — | — | 10 |
|  | 0.5 | — | — | — | — | 9 |
|  | acet. | 8 | 2 | — | — | — |
|  | cont. | 7 | 3 | — | — | — |
| MWB | 10 | — | — | — | 5 | |
|  | 1 | — | — | — | 10 | |
|  | 0.5 | — | — | — | 10 | |
|  | acet. | 10 | — | — | — | |
|  | cont. | 10 | — | — | — | |
| WM | 10 | 7 | 2 | — | 1 | |
|  | 1 | 9 | — | — | 1 | |
|  | 0.5 | 8 | 1 | — | — | |
|  | cont. | 8 | — | — | 2 | |
| MBB | 10 | — | — | — | 1 | |
|  | 1 | — | — | — | 10 | |
|  | 0.5 | — | — | — | 9 | |
|  | acet. | 10 | — | — | — | |
|  | cont. | 10 | — | — | — | |

3-METHYL-7-ETHYL-10-(3,4-METHYLENEDIOXYPHENYL)-3,7-DECADIENE

| Insect | Conc.,% | 0 | 1 | 2 | 3 | 4 |
|---|---|---|---|---|---|---|
| Tenebrio | 10 | — | — | — | — | 10 |
|  | 1 | — | — | — | 1 | 9 |
|  | 0.5 | — | — | — | 2 | 8 |
|  | acet. | 9 | 1 | — | — | — |
|  | cont. | 9 | 1 | — | — | — |
| MWB | 10 | — | — | — | 10 | |
|  | 1 | 7 | — | 2 | 1 | |
|  | 0.5 | 9 | 1 | — | — | |
|  | acet. | 10 | — | — | — | |
|  | cont. | 9 | — | — | — | |
| WM | 10 | 10 | — | — | — | |
|  | 1 | 10 | — | — | — | |
|  | 0.5 | 9 | — | — | — | |

-continued
3-METHYL-7-ETHYL-10-(3,4-METHYLENEDIOXYPHENYL)-3,7-DECADIENE

| Insect | Conc.,% | 0 | 1 | 2 | 3 | 4 |
|---|---|---|---|---|---|---|
|  | acet. | 9 | — | — | — | |
|  | cont. | 8 | — | — | — | |
| MBB | 10 | — | — | — | 10 | |
|  | 1 | — | — | — | 10 | |
|  | 0.5 | — | — | 1 | 9 | |
|  | acet. | 10 | — | — | — | |
|  | cont. | 9 | — | — | — | |

2,6-DIMETHYL-9-(3-METHOXYPHENYL)-2,6-NONADIENE

| Insect | Conc.,% | 0 | 1 | 2 | 3 | 4 |
|---|---|---|---|---|---|---|
| Tenebrio | 10 | — | — | — | — | 10 |
|  | 1 | — | — | — | — | 10 |
|  | 0.5 | — | — | — | 1 | 9 |
|  | acet. | 7 | 3 | — | — | — |
|  | cont. | 8 | 2 | — | — | — |
| MWB | 10 | — | — | — | 9 | |
|  | 1 | — | 1 | 5 | 3 | |
|  | 0.5 | 3 | 3 | 4 | — | |
|  | acet. | 10 | — | — | — | |
|  | cont. | 10 | — | — | — | |
| WM | 10 | 9 | — | 1 | — | |
|  | 1 | 9 | — | — | — | |
|  | 0.5 | 10 | — | — | — | |
|  | acet. | 10 | — | — | — | |
|  | cont. | 10 | — | — | — | |
| MBB | 10 | — | — | — | 3 | |
|  | 1 | 10 | — | — | — | |
|  | 0.5 | 10 | — | — | — | |
|  | acet. | 10 | — | — | — | |
|  | cont. | 10 | — | — | — | |

2,6-DIMETHYL-9-(4-METHOXYPHENYL)-2,6-NONADIENE

| Insect | Conc.,% | 0 | 1 | 2 | 3 | 4 |
|---|---|---|---|---|---|---|
| Tenebrio | 10 | NOT TESTED | | | | |
|  | 1 | — | 1 | 2 | 5 | 2 |
|  | 0.5 | 1 | 6 | 3 | — | — |
|  | acet. | 7 | 3 | — | — | — |
|  | cont. | 6 | 4 | — | — | — |
| MWB | 10 | NOT TESTED | | | | |
|  | 1 | 5 | 5 | — | — | |
|  | 0.5 | 10 | — | — | — | |
|  | acet. | 10 | — | — | — | |
|  | cont. | 10 | — | — | — | |
| WM | 10 | 10 | — | — | — | |
|  | 1 | 9 | — | — | — | |
|  | 0.5 | 10 | — | — | — | |
|  | acet. | 10 | — | — | — | |
|  | cont. | 10 | — | — | — | |
| MBB | 10 | 6 | 1 | 3 | — | |
|  | 1 | 10 | — | — | — | |
|  | 0.5 | 10 | — | — | — | |
|  | acet. | 9 | 1 | — | — | |
|  | cont. | 10 | — | — | — | |

2,6-DIMETHYL-9-(3,4-DIMETHOXYPHENYL)-2,6-NONADIENE

| Insect | Conc.,% | 0 | 1 | 2 | 3 | 4 |
|---|---|---|---|---|---|---|
| Tenebrio | 10 | 2 | 5 | 3 | — | — |
|  | 1 | 4 | 5 | — | — | — |
|  | 0.5 | 10 | — | — | — | — |
|  | acet. | 5 | 2 | — | — | — |
|  | cont. | 9 | 1 | — | — | — |
| MWB | 10 | — | — | 3 | 2 | |
|  | 1 | 8 | — | — | — | |
|  | 0.5 | 8 | — | — | — | |
|  | acet. | 9 | — | — | — | |
|  | cont. | 9 | — | — | — | |
| WM | 10 | 10 | — | — | — | |
|  | 1 | 10 | — | — | — | |
|  | 0.5 | 10 | — | — | — | |
|  | acet. | 10 | — | — | — | |
|  | cont. | 10 | — | — | — | |
| MBB | 10 | — | 3 | — | — | |

-continued
2,6-DIMETHYL-9-(3,4-DIMETHOXYPHENYL)-2,6-NONADIENE

| Insect | Conc.,% | 0 | 1 | 2 | 3 | 4 |
|---|---|---|---|---|---|---|
|  | 1 | 10 | — | — | — |  |
|  | 0.5 | 10 | — | — | — |  |
|  | acet. | 8 | 1 | — | — |  |
|  | cont. | 9 | — | — | — |  |

3,4-EPOXY-3,7-DIMETHYL-10-(3,4-METHYLENE-DIOXYPHENYL)-7-DECENE

| Insect | Conc.,% | 0 | 1 | 2 | 3 | 4 |
|---|---|---|---|---|---|---|
| Tenebrio | 10 | — | — | — | — | 10 |
|  | 1 | — | — | — | — | 10 |
|  | 0.5 | — | — | — | — | 10 |
|  | acet. | 10 | — | — | — | — |
|  | cont. | 9 | — | — | — | 1 |
| MWB | 1 | 2 | — | — | 8 |  |
|  | 0.5 | 2 | 5 | 2 | — |  |
|  | acet. | 10 | — | — | — |  |
|  | cont. | 10 | — | — | — |  |
| WM | 1 | — | — | — | 10 |  |
|  | 0.5 | — | — | 1 | 9 |  |
|  | acet. | 10 | — | — | — |  |
|  | cont. | 10 | — | — | — |  |
| MBB | 1 | — | — | — | 10 |  |
|  | 0.5 | — | — | — | 10 |  |
|  | acet. | 10 | — | — | — |  |
|  | cont. | 10 | — | — | — |  |

3,4-EPOXY-3-METHYL-7-ETHYL-10-(3,4-METHYLENE-DIOXYPHENYL)-7-DECENE

| Insect | Conc.,% | 0 | 1 | 2 | 3 | 4 |
|---|---|---|---|---|---|---|
| Tenebrio | 1 | — | — | — | — | 10 |
|  | 0.5 | — | — | — | — | 10 |
|  | acet. | 8 | — | — | — | — |
|  | cont. | 9 | — | — | — | — |
| MWB | 1 | — | — | — | 8 |  |
|  | 0.5 | — | — | — | 9 |  |
|  | acet. | 10 | — | — | — |  |
|  | cont. | 10 | — | — | — |  |
| WM | 1 | — | — | — | 10 |  |
|  | 0.5 | 1 | — | — | 9 |  |
|  | acet. | 10 | — | — | — |  |
|  | cont. | 10 | — | — | — |  |
| MBB | 1 | — | — | — | 10 |  |
|  | 0.5 | — | — | — | 10 |  |
|  | acet. | 10 | — | — | — |  |
|  | cont. | 10 | — | — | — |  |

2,6-DICHLORO-2,6-DIMETHYL-9-(3,4-METHYLENEDIOXYPHENYL)NONANE

| Insect | Conc.,% | 0 | 1 | 2 | 3 | 4 |
|---|---|---|---|---|---|---|
| Tenebrio | 10 | — | — | 1 | 9 | — |
|  | 1 | — | — | 10 | — | — |
|  | 0.5 | — | 2 | 8 | — | — |
|  | acet. | 6 | 3 | 1 | — | — |
|  | cont. | 9 | 1 | — | — | — |
| MWB | 10 | — | — | — | 5 |  |
|  | 1 | — | — | — | 10 |  |
|  | 0.5 | — | — | — | 8 |  |
|  | acet. | 10 | — | — | — |  |
|  | cont. | 9 | — | — | — |  |
| WM | 10 | 10 | — | — | — |  |
|  | 1 | 10 | — | — | — |  |
|  | 0.5 | 10 | — | — | — |  |
|  | acet. | 10 | — | — | — |  |
|  | cont. | 10 | — | — | — |  |
| MBB | 10 | — | 1 | 4 | 5 |  |
|  | 1 | 5 | 3 | 2 | — |  |
|  | 0.5 | 8 | 2 | — | — |  |
|  | acet. | 9 | 1 | — | — |  |
|  | cont. | 10 | — | — | — |  |

2,6-DIMETHYL-9-(3,4-METHYLENEDIOXYPHENYL)-6-NONENE

| Insect | Conc.,% | 0 | 1 | 2 | 3 | 4 |
|---|---|---|---|---|---|---|
| Tenebrio | 10 | 1 | — | — | — | 9 |
|  | 1 | — | — | 4 | — | 6 |
|  | 0.5 | 3 | 1 | 2 | 2 | 2 |
|  | acet. | 9 | 1 | — | — | — |
|  | cont. | 10 | — | — | — | — |
| MWB | 10 | — | — | — | 7 |  |
|  | 1 | 1 | — | — | 8 |  |
|  | 0.5 | 5 | 1 | — | 3 |  |
|  | acet. | 9 | 1 | — | — |  |
|  | cont. | 10 | — | — | — |  |
| WM | 10 | 10 | — | — | — |  |
|  | 1 | 9 | 1 | — | — |  |
|  | 0.5 | 9 | 1 | — | — |  |
|  | acet. | 9 | 1 | — | — |  |
|  | cont. | 9 | 1 | — | — |  |
| MBB | 10 | — | — | — | 10 |  |
|  | 1 | — | — | — | 10 |  |
|  | 0.5 | — | 1 | 7 | 2 |  |
|  | acet. | 9 | 1 | — | — |  |
|  | cont. | 10 | — | — | — |  |

9-(3-ETHOXYPHENYL)-2,6-DIMETHYL-2,6-NONADIENE

| Insect | Conc.,% | 0 | 1 | 2 | 3 | 4 |
|---|---|---|---|---|---|---|
| Tenebrio | 10 | — | 1 | — | 5 | 4 |
|  | 1 | 8 | 2 | — | — | — |
|  | 0.5 | 10 | — | — | — | — |
|  | acet. | 10 | — | — | — | — |
|  | cont. | 9 | 1 | — | — | — |
| MWB | 10 | — | — | — | 7 |  |
|  | 1 | — | — | 7 | 2 |  |
|  | 0.5 | 3 | 1 | 2 | — |  |
|  | acet. | 8 | 1 | — | — |  |
|  | cont. | 9 | 1 | — | — |  |
| WM | 10 | 10 | — | — | — |  |
|  | 1 | 10 | — | — | — |  |
|  | 0.5 | 10 | — | — | — |  |
|  | acet. | 10 | — | — | — |  |
|  | cont. | 10 | — | — | — |  |
| MBB | 10 | 1 | — | 2 | 7 |  |
|  | 1 | 8 | 2 | — | — |  |
|  | 0.5 | 10 | — | — | — |  |
|  | acet. | 9 | 1 | — | — |  |
|  | cont. | 9 | — | — | — |  |

9-(2-CHLORO-4,5-METHYLENEDIOXYPHENYL)-2,6-DIMETHYL-2,6-NONADIENE

| Insect | Conc.,% | 0 | 1 | 2 | 3 | 4 |
|---|---|---|---|---|---|---|
| Tenebrio | 10 | 10 | — | — | — | — |
|  | 1 | 10 | — | — | — | — |
|  | 0.5 | 10 | — | — | — | — |
|  | acet. | 10 | — | — | — | — |
|  | cont. | 10 | — | — | — | — |
| MWB | 10 | — | — | — | 10 |  |
|  | 1 | 3 | 1 | — | 6 |  |
|  | 0.5 | 9 | 1 | — | — |  |
|  | acet. | 10 | — | — | — |  |
|  | cont. | 10 | — | — | — |  |
| WM | 10 | 8 | — | 1 | — |  |
|  | 1 | 10 | — | — | — |  |
|  | 0.5 | 10 | — | — | — |  |
|  | acet. | 10 | — | — | — |  |
|  | cont. | 10 | — | — | — |  |
| MBB | 10 | 7 | 3 | — | 10 |  |
|  | 1 | 9 | — | 1 | 10 |  |
|  | 0.5 | 10 | — | — | — |  |
|  | acet. | 10 | — | — | — |  |
|  | cont. | 10 | — | — | — |  |

2,6-DIMETHYL-9-PHENYL-2,6-NONADIENE

| Insect | Conc.,% | 0 | 1 | 2 | 3 | 4 |
|---|---|---|---|---|---|---|
| Tenebrio | 10 | — | — | 1 | 4 | 5 |
|  | 1 | 6 | 4 | — | — | — |

-continued
2,6-DIMETHYL-9-PHENYL-2,6-NONADIENE

| Insect | Conc.,% | 0 | 1 | Rating 2 | 3 | 4 |
|---|---|---|---|---|---|---|
|  | 0.5 | 7 | 3 | — | — | — |
|  | acet. | 10 | — | — | — | — |
|  | cont. | 9 | 1 | — | — | — |
| MWB | 10 | — | — | — | 9 | — |
|  | 1 | 2 | 1 | — | — | — |
|  | 0.5 | 8 | 1 | 1 | — | — |
|  | acet. | 10 | — | — | — | — |
|  | cont. | 10 | — | — | — | — |
| WM | 10 | 10 | — | — | — | — |
|  | 1 | 10 | — | — | — | — |
|  | 0.5 | 10 | — | — | — | — |
|  | acet. | 10 | — | — | — | — |
|  | cont. | 10 | — | — | — | — |
| MBB | 10 | — | — | — | 10 | — |
|  | 1 | — | — | — | 10 | — |
|  | 0.5 | — | — | — | 10 | — |
|  | acet. | 10 | — | — | — | — |
|  | cont. | 8 | 1 | — | — | — | trans-9-(4-CHLOROPHENYL)-2,6-DIMETHYL-2,6-NONADIENE

| Insect | Conc.,% | 0 | 1 | Rating 2 | 3 | 4 |
|---|---|---|---|---|---|---|
| Tenebrio | 10 | — | — | — | — | 10 |
|  | 1 | 4 | 3 | — | 3 | — |
|  | 0.5 | 10 | — | — | — | — |
|  | acet. | 10 | — | — | — | — |
|  | cont. | 10 | — | — | — | — |
| MWB | 10 | — | — | — | 10 | — |
|  | 1 | — | — | — | 10 | — |
|  | 0.5 | — | — | — | 10 | — |
|  | acet. | 10 | — | — | — | — |
|  | cont. | 10 | — | — | — | — |
| WM | 10 | 6 | 1 | 3 | — | — |
|  | 1 | 9 | — | 1 | — | — |
|  | 0.5 | 10 | — | — | — | — |
|  | acet. | 10 | — | — | — | — |
|  | cont. | 10 | — | — | — | — |
| MBB | 10 | — | — | — | 10 | — |
|  | 1 | — | — | — | 10 | — |
|  | 0.5 | — | — | — | 10 | — |
|  | acet. | 10 | — | — | — | — |
|  | cont. | 10 | — | — | — | — | trans-9-(3-CHLOROPHENYL)-2,6-DIMETHYL-2,6-NONADIENE

| Insect | Conc.,% | 0 | 1 | Rating 2 | 3 | 4 |
|---|---|---|---|---|---|---|
| Tenebrio | 10 | 2 | 1 | 1 | 6 | — |
|  | 1 | 10 | — | — | — | — |
|  | 0.5 | 10 | — | — | — | — |
|  | acet. | 10 | — | — | — | — |
|  | cont. | 10 | — | — | — | — |
| MWB | 10 | — | — | — | 10 | — |
|  | 1 | — | — | — | 10 | — |
|  | 0.5 | — | — | — | 10 | — |
|  | acet. | 10 | — | — | — | — |
|  | cont. | 10 | — | — | — | — |
| WM | 10 | 7 | 3 | — | — | — |
|  | 1 | 7 | 1 | 2 | — | — |
|  | 0.5 | 10 | — | — | — | — |
|  | acet. | 10 | — | — | — | — |
|  | cont. | 10 | — | — | — | — |
| MBB | 10 | — | — | — | 10 | — |
|  | 1 | 9 | — | — | — | 1 |
|  | 0.5 | 10 | — | — | — | — |
|  | acet. | 10 | — | — | — | — |
|  | cont. | 10 | — | — | — | — | trans-ETHYL p-(4,8-DIMETHYL-3,7-NONADIENYL)BENZOATE

| Insect | Conc.,% | 0 | 1 | Rating 2 | 3 | 4 |
|---|---|---|---|---|---|---|
| Tenebrio | 10 | 3 | 5 | 1 | 1 | — |
|  | 1 | 10 | — | — | — | — |
|  | 0.5 | 9 | — | — | — | — |

-continued
trans-ETHYL p-(4,8-DIMETHYL-3,7-NONADIENYL)BENZOATE

| Insect | Conc.,% | 0 | 1 | Rating 2 | 3 | 4 |
|---|---|---|---|---|---|---|
|  | acet. | 9 | — | — | — | — |
|  | cont. | 10 | — | — | — | — |
| MWB | 10 | — | — | — | 10 | — |
|  | 1 | — | — | — | 10 | — |
|  | 0.5 | 1 | — | 3 | 6 | — |
|  | acet. | 10 | — | — | — | — |
|  | cont. | 10 | — | — | — | — |
| WM | 10 | 10 | — | — | — | — |
|  | 1 | 10 | — | — | — | — |
|  | 0.5 | 10 | — | — | — | — |
|  | acet. | 10 | — | — | — | — |
|  | cont. | 10 | — | — | — | — |
| MBB | 10 | 8 | — | 2 | — | — |
|  | 1 | 10 | — | — | — | — |
|  | 0.5 | 9 | — | — | — | — |
|  | acet. | 10 | — | — | — | — |
|  | cont. | 8 | — | — | — | — | trans-9-(2,6-DICHLOROPHENYL)-2,6-DIMETHYL-2,6-NONADIENE

| Insect | Conc.,% | 0 | 1 | Rating 2 | 3 | 4 |
|---|---|---|---|---|---|---|
| Tenebrio | 10 | 9 | — | — | — | — |
|  | 1 | 10 | — | — | — | — |
|  | 0.5 | 10 | — | — | — | — |
|  | acet. | 10 | — | — | — | — |
|  | cont. | 10 | — | — | — | — |
| MWB | 10 | — | — | — | 10 | — |
|  | 1 | 8 | — | — | — | — |
|  | 0.5 | 10 | — | — | — | — |
|  | acet. | 10 | — | — | — | — |
|  | cont. | 9 | — | — | — | — |
| WM | 10 | 10 | — | — | — | — |
|  | 1 | 10 | — | — | — | — |
|  | 0.5 | 10 | — | — | — | — |
|  | acet. | 10 | — | — | — | — |
|  | cont. | 10 | — | — | — | — |
| MBB | 10 | 8 | 2 | — | — | — |
|  | 1 | 9 | 1 | — | — | — |
|  | 0.5 | 10 | — | — | — | — |
|  | acet. | 10 | — | — | — | — |
|  | cont. | 10 | — | — | — | — | trans-2,6-DIMETHYL-9-(m-TOLYL)-2,6-NONADIENE

| Insect | Conc.,% | 0 | 1 | Rating 2 | 3 | 4 |
|---|---|---|---|---|---|---|
| Tenebrio | 10 | — | — | — | — | 10 |
|  | 1 | 9 | — | 1 | — | — |
|  | 0.5 | 10 | — | — | — | — |
|  | acet. | 10 | — | — | — | — |
|  | cont. | 9 | — | — | — | — |
| MWB | 10 | — | — | — | 10 | — |
|  | 1 | 5 | — | 2 | 1 | — |
|  | 0.5 | 10 | — | — | — | — |
|  | acet. | 9 | — | — | — | — |
|  | cont. | 9 | — | — | — | — |
| WM | 10 | 10 | — | — | — | — |
|  | 1 | 10 | — | — | — | — |
|  | 0.5 | 10 | — | — | — | — |
|  | acet. | 10 | — | — | — | — |
|  | cont. | 10 | — | — | — | — |
| MBB | 10 | — | — | — | 10 | — |
|  | 1 | 1 | 1 | 1 | 7 | — |
|  | 0.5 | 9 | — | 1 | — | — |
|  | acet. | 10 | — | — | — | — |
|  | cont. | 10 | — | — | — | — | trans-4-(4,8-DIMETHYL-3,7-NONADIENYL)-N,N-DIMETYLANILINE

| Insect | Conc., | 0 | 1 | Rating 2 | 3 | 4 |
|---|---|---|---|---|---|---|
| Tenebrio | 10 | — | — | — | — | 10 |
|  | 1 | 2 | 2 | 1 | 4 | — |
|  | 0.5 | 10 | — | — | — | — |
|  | acet. | 10 | — | — | — | — |

-continued trans-4-(4,8-DIMETHYL-3,7-NONADIENYL)-N,N-DIMETYLANILINE

| Insect | Conc., | 0 | 1 | Rating 2 | 3 | 4 |
|---|---|---|---|---|---|---|
| | cont. | 10 | — | — | — | — |
| MWB | 10 | — | — | — | 10 | — |
| | 1 | 5 | 1 | 1 | 2 | |
| | 0.5 | 10 | — | — | — | |
| | acet. | 10 | — | — | — | |
| | cont. | 10 | — | — | — | |
| WM | 10 | 10 | — | — | — | |
| | 1 | 10 | — | — | — | |
| | 0.5 | 10 | — | — | — | |
| | acet. | 10 | — | — | — | |
| | cont. | 10 | — | — | — | |
| MBB | 10 | — | — | — | 10 | |
| | 1 | 9 | — | — | 1 | |
| | 0.5 | 10 | — | — | — | |
| | acet. | 10 | — | — | — | |
| | cont. | 10 | — | — | — | | trans-9-(2-THIENYL)-2,6-DIMETHYL-2,6-NONADIENE

| Insect | Conc.,% | 0 | 1 | Rating 2 | 3 | 4 |
|---|---|---|---|---|---|---|
| Tenebrio | 10 | — | 1 | — | — | 9 |
| | 1 | 10 | — | — | — | — |
| | 0.5 | 8 | 2 | — | — | — |
| | acet. | 9 | — | — | — | — |
| | cont. | 8 | 1 | — | — | — |
| MWB | 10 | 3 | — | — | 4 | |
| | 1 | 10 | — | — | — | |
| | 0.5 | 10 | — | — | — | |
| | acet. | 10 | — | — | — | |
| | cont. | 10 | — | — | — | |
| WM | 10 | | | | | |
| | 1 | | | | | |
| | 0.5 | | NOT TESTED | | | |
| | acet. | | | | | |
| | cont. | | | | | |
| MBB | 10 | — | — | — | 10 | |
| | 1 | 5 | 5 | — | — | |
| | 0.5 | 9 | 1 | — | — | |
| | acet. | 9 | — | — | 1 | |
| | cont. | 9 | — | — | — | | trans-9-(3-BROMOPHENYL)-2,6-DIMETHYL-2,6-NONADIENE

| Insect | Conc.,% | 0 | 1 | Rating 2 | 3 | 4 |
|---|---|---|---|---|---|---|
| Tenebrio | 10 | 8 | 2 | — | — | — |
| | 1 | 8 | 2 | — | — | — |
| | 0.5 | 8 | 1 | 1 | — | — |
| | acet. | 10 | — | — | — | — |
| | cont. | 10 | — | — | — | — |
| MWB | 10 | — | — | — | 10 | — |
| | 1 | — | — | — | 10 | |
| | 0.5 | — | — | — | 10 | |
| | acet. | 10 | — | — | — | |
| | cont. | 10 | — | — | — | |
| WM | 10 | | | | | |
| | 1 | | | | | |
| | 0.5 | | NOT TESTED | | | |
| | acet. | | | | | |
| | cont. | | | | | |
| MBB | 10 | 9 | — | — | 1 | |
| | 1 | 7 | 1 | — | 2 | |
| | 0.5 | 8 | 1 | — | 1 | |
| | acet. | 8 | 2 | — | — | |
| | cont. | 10 | — | — | — | | trans-9-(4-BROMOPHENYL)-2,6-DIMETHYL-2,6-NONADIENE

| Insect | Conc.,% | 0 | 1 | Rating 2 | 3 | 4 |
|---|---|---|---|---|---|---|
| Tenebrio | 10 | — | — | — | — | 10 |
| | 1 | 9 | 1 | — | — | — |
| | 0.5 | 8 | 1 | — | — | 1 |
| | acet. | 10 | — | — | — | — |
| | cont. | 10 | — | — | — | — | trans-9-(4-BROMOPHENYL)-2,6-DIMETHYL-2,6-NONADIENE

| Insect | Conc.,% | 0 | 1 | Rating 2 | 3 | 4 |
|---|---|---|---|---|---|---|
| MWB | 10 | — | — | — | 9 | |
| | 1 | — | — | — | 10 | |
| | 0.5 | — | — | — | 10 | |
| | acet. | 10 | — | — | — | |
| | cont. | 10 | — | — | — | |
| WM | 10 | | | | | |
| | 1 | | | | | |
| | 0.5 | | NOT TESTED | | | |
| | acet. | | | | | |
| | cont. | | | | | |
| MBB | 10 | — | — | — | 10 | |
| | 1 | — | — | — | 10 | |
| | 0.5 | — | — | — | 10 | |
| | acet. | 10 | — | — | — | |
| | cont. | 10 | — | — | — | | trans-9-(4-FLUOROPHENYL)-2,6-DIMETHYL-2,6-NONADIENE

| Insect | Conc.,% | 0 | 1 | Rating 2 | 3 | 4 |
|---|---|---|---|---|---|---|
| Tenebrio | 10 | — | — | — | — | 10 |
| | 1 | 10 | — | — | — | — |
| | 0.5 | 10 | — | — | — | — |
| | acet. | 9 | — | — | — | — |
| | cont. | 10 | — | — | — | — |
| MWB | 10 | — | — | — | 10 | |
| | 1 | — | — | 2 | 8 | |
| | 0.5 | — | — | 3 | 7 | |
| | acet. | 9 | — | — | — | |
| | cont. | 10 | — | — | — | |
| WM | 10 | 10 | — | — | — | |
| | 1 | 9 | — | — | — | |
| | 0.5 | 10 | — | — | — | |
| | acet. | 10 | — | — | — | |
| | cont. | 10 | — | — | — | |
| MBB | 10 | — | — | — | 10 | |
| | 1 | — | — | — | 10 | |
| | 0.5 | — | — | — | 10 | |
| | acet. | 10 | — | — | — | |
| | cont. | 10 | — | — | — | | trans-4-(4,8-DIMETHYL-3,7-NONADIENYL)BENZONITRILE

| Insect | Conc.,% | 0 | 1 | Rating 2 | 3 | 4 |
|---|---|---|---|---|---|---|
| Tenebrio | 10 | 9 | — | — | — | 1 |
| | 1 | 10 | — | — | — | — |
| | 0.5 | 10 | — | — | — | — |
| | acet. | 10 | — | — | — | — |
| | cont. | 10 | — | — | — | — |
| MWB | 10 | — | — | — | 10 | |
| | 1 | — | — | 3 | 7 | |
| | 0.5 | 3 | 5 | 1 | 1 | |
| | acet. | 10 | — | — | — | |
| | cont. | 10 | — | — | — | |
| WM | 10 | 10 | — | — | — | |
| | 1 | 10 | — | — | — | |
| | 0.5 | 10 | — | — | — | |
| | acet. | 10 | — | — | — | |
| | cont. | 10 | — | — | — | |
| MBB | 10 | 10 | — | — | — | |
| | 1 | 10 | — | — | — | |
| | 0.5 | 10 | — | — | — | |
| | acet. | 10 | — | — | — | |
| | cont. | 10 | — | — | — | | trans-9-(3,4-DICHLOROPHENYL)-2,6-DIMETHYL-2,6-NONADIENE

| Insect | Conc.,% | 0 | 1 | Rating 2 | 3 | 4 |
|---|---|---|---|---|---|---|
| Tenebrio | 10 | 10 | — | — | — | — |
| | 1 | 10 | — | — | — | — |
| | 0.5 | 10 | — | — | — | — |
| | acet. | 10 | — | — | — | — |
| | cont. | 10 | — | — | — | — |

-continued
trans-9-(3,4-DICHLOROPHENYL)-2,6-DIMETHYL-2,6-NONADIENE

| Insect | Conc.,% | 0 | 1 | Rating 2 | 3 | 4 |
|---|---|---|---|---|---|---|
| MWB | 10 | — | — | — | — | 10 |
| | 1 | — | — | — | — | 10 |
| | 0.5 | — | — | — | — | 10 |
| | acet. | 10 | — | — | — | — |
| | cont. | 10 | — | — | — | — |
| WM | 10 | 10 | — | — | — | — |
| | 1 | 10 | — | — | — | — |
| | 0.5 | 10 | — | — | — | — |
| | acet. | 10 | — | — | — | — |
| | cont. | 10 | — | — | — | — |
| MBB | 10 | 6 | 1 | 1 | — | 2 |
| | 1 | 10 | — | — | — | — |
| | 0.5 | 10 | — | — | — | — |
| | acet. | 10 | — | — | — | — |
| | cont. | 10 | — | — | — | — |

Additional compounds in this series were tested against one or two of the insect species and were shown to be active against such species. The results of these tests are summarized in the following tables.

2,6-DIMETHYL-9-(3,4-ETHYLENEDIOXYPHENYL)-2,6-NONADIENE

| Insect | Conc.,% | 0 | 1 | Rating 2 | 3 | 4 |
|---|---|---|---|---|---|---|
| Tenebrio | 10 | — | — | — | — | 10 |
| | 1 | — | — | — | 2 | 8 |
| | 0.5 | — | — | — | — | 10 |
| | acet. | 10 | — | — | — | — |
| | cont. | 10 | — | — | — | — |

3,7-DIMETHYL-10-(3,4-METHYLENEDIOXYPHENYL)-3,7-DECADIENE

| Insect | Conc.,% | 0 | 1 | Rating 2 | 3 | 4 |
|---|---|---|---|---|---|---|
| Tenebrio | 10 | — | — | — | — | 10 |
| | 1 | — | — | — | — | 10 |
| | 0.5 | — | — | — | — | 10 |
| | acet. | 8 | 2 | — | — | — |
| | cont. | NOT TESTED | | | | |
| MWB | 10 | — | — | — | — | 5 |
| | 1 | — | — | — | — | 9 |
| | 0.5 | — | 1 | — | — | 8 |
| | acet. | 9 | — | — | — | — |
| | cont. | NOT TESTED | | | | |

2,3-EPOXY-2,6-DIMETHYL-9-(3,4-METHYLENEDIOXYPHENYL)-6-NONENE

| Insect | Conc.,% | 0 | 1 | Rating 2 | 3 | 4 |
|---|---|---|---|---|---|---|
| Tenebrio | 10 | — | — | — | — | 10 |
| | 1 | 1 | — | — | — | 9 |
| | 0.5 | — | — | — | — | 10 |
| | acet. | 7 | 3 | — | — | — |
| | cont. | 10 | — | — | — | — |
| MWB | 10 | — | — | — | — | 7 |
| | 1 | — | 5 | — | — | 2 |
| | 0.5 | — | 2 | 4 | — | — |
| | acet. | 6 | — | — | — | — |
| | cont. | NOT TESTED | | | | |

2,6-DIMETHYL-9-(3,4-METHYLENEDIOXYPHENYL)NONANE

| Insect | Conc.,% | 0 | 1 | Rating 2 | 3 | 4 |
|---|---|---|---|---|---|---|
| Tenebrio | 10 | — | — | — | — | 10 |
| | 1 | — | — | — | — | 10 |
| | 0.5 | — | — | — | 3 | 7 |
| | acet. | 7 | 3 | — | — | — |

-continued
2,6-DIMETHYL-9-(3,4-METHYLENEDIOXYPHENYL)NONANE

| Insect | Conc.,% | 0 | 1 | Rating 2 | 3 | 4 |
|---|---|---|---|---|---|---|
| | cont. | 7 | 3 | — | — | — |
| MWB | 10 | — | — | — | 8 | — |
| | 1 | — | — | — | 10 | — |
| | 0.5 | — | — | — | 8 | — |
| | acet. | 9 | — | — | — | — |
| | cont. | 7 | — | — | — | — |

5-(n-NONYL)-1,3-BENZODIOXOLE

| Insect | Conc.,% | 0 | 1 | Rating 2 | 3 | 4 |
|---|---|---|---|---|---|---|
| Tenebrio | 10 | — | — | — | 3 | 7 |
| | 1 | 2 | — | 5 | 1 | 1 |
| | 0.5 | 6 | 1 | 3 | — | — |
| | acet. | 10 | — | — | — | — |
| | cont. | 10 | — | — | — | — |
| MWB | 10 | 4 | — | 1 | 5 | — |
| | 1 | 3 | 1 | 1 | 4 | — |
| | 0.5 | 8 | 1 | — | — | — |
| | acet. | 10 | — | — | — | — |
| | cont. | 10 | — | — | — | — |
| MBB | 10 | — | — | — | 8 | — |
| | 1 | 10 | — | — | — | — |
| | 0.5 | 9 | — | — | — | — |
| | acet. | 10 | — | — | — | — |
| | cont. | 10 | — | — | — | — |

Various of the compounds of this invention have been tested against several insect species representing a number of insect orders to demonstrate their versatility and broad spectrum activity. Since the test methods used and different for different insects, each insect test will be described separately.

Mosquito

Two compounds, 7,8-epoxy-4-ethyl-8-methyl-1-(3,4-methylenedioxyphenyl)-3-decene and 2,6-diemthyl-9-(3,4-methylenedioxyphenyl)-2,6-nonadiene, were tested against *Aedes aegypti* mosquito larvae in aqueous solutions at concentrations of 10, 5, 2.5. 1.25 and 0.625 ppm. each. Ninety milliliters of each solution were placed in a pint jar and 30 five-day-old mosquito larvae were added to each jar. Two tests were run at each concentration and control tests employing only solvent with no compound were also run. Food was added to each jar, the jars were covered with cloths, and maintained at 29°C. until adults emerged in the control jars. The number of adults in the test jars was determined. The results 13 days after the test started are summarized in the following table.

| Compound | Conc., ppm. | Jar 1 Living | Dead | Jar 2 Living | Dead |
|---|---|---|---|---|---|
| Nonadiene | 10 | 0 | 0 | 0 | 0 |
| | 5 | 0 | 0 | 0 | 0 |
| | 2.5 | 0 | 0 | 0 | 1 |
| | 1.25 | 3 | 1 | 1 | 10 |
| | 0.625 | 1 | 21 | 0 | 21 |
| Decene | 10 | 0 | 0 | 0 | 0 |
| | 5 | 0 | 0 | 0 | 0 |
| | 2.5 | 0 | 0 | 0 | 0 |
| | 1.25 | 0 | 0 | 0 | 0 |
| | 0.625 | 0 | 0 | 0 | 0 |
| Control | — | 2 | 21 | 0 | 28 |
| | — | 3 | 23 | 0 | 28 |

The nonadiene gave 100 percent control at concentrations as low as 25 ppm. The decene gave 100 percent control at concentrations as low as 0.625 ppm. Live adults were observed in the control jars 6 days after the start of the test. There were never any live adults in the nonadiene jars at concentrations of 10, 5, and 2.5 ppm. nor in the decene jars at any concentration.

Southern Corn Rootworm

Petri dishes containing 150 g. of sand were autoclaved for one hour. Corn seed which had been soaked overnight was rinsed first with a solution of 10 percent alcohol, 20 percent chlorox, and 70 percent water for 15 minutes and then with clear water. Three to four seeds were placed in each dish. The dishes were then moistened with 15 ml. of a 100 ppm. solution of a fungicide. After 24 hours, ten Southern corn rootworm eggs (*Diabrotica undecimpunctata*) were placed in each dish. The dishes were maintained in an incubator in the dark for 14 days. New petri dishes were prepared as described except that the eggs were not added and 2,6-diemthyl-9-(3,4-methylenedioxyphenyl)-2,6-nonadiene was added at a rate of 100 ppm. or 10 ppm. Ten dishes at each treatment rate and ten controls were used. Three larvae from the incubated dishes were placed in each of the treated dishes and each control dish. After 21 days, no adults had emerged in the dishes treated at 100 ppm. There were a total of 15 adults in the ten dishes treated at 10 ppm. and a total of 19 adults in the ten control dishes.

German Cockroach

Test jars were prepared by adding 2 ml. of an acetone solution containing 10 mg., 20 mg., or 100 mg. of 2,6-dimethyl-9-(3,4-methylenedioxyphenyl)-2,6-nonadiene to 1 gallon glass jars and allowing the acetone to evaporate. The jars were equipped with watering bottles, food, and paper towels. There were two jars for each rate of test compound and two jars for nontreated controls. To each jar were added 20 40-day-old cockroach nymphs (*Blattella germanica*). After about 2½ months, the 100 mg. jars did not contain newly hatched nymphs and all adults in the jars had deformed wings. The control jars and the 10 and 20 mg. jars contained normal adults and newly hatched nymphs. Four months after the test had started, the roaches in the 100 mg. jars showed no reproduction while the control jars and lower rate jars had produced large numbers of newly hatched nymphs. Thus, the nonadiene at 100 mg. had prevented reproduction for 4 months.

In another test, the nonadiene was applied topically to 50-day-old German cockroach nymphs. The compound was applied in acetone as a 10 percent, or 0.5 percent solution. Acetone controls and nontreated controls were also run. The roaches were then maintained in the laboratory until the controls reproduced. Those treated with the 10 percent solution had normal wing formation but did not reproduce. The 1 percent and 0.5 percent treatments did reproduce.

Housefly

Test compounds were mixed with the rearing diet of houseflys at various levels. The prepared diet was then placed in an 8 oz. drinking cup. Three cups were prepared for each treatment level and three control cups. Housefly eggs (*Musca domestica*) were placed in each cup and they were maintained at 28°C. for 1 week. Fifty pupae were then removed from each cup and placed in a petri dish. After the control pupae had emerged into adults, the percent emergence in each dish was recorded. The test compounds used were 7,8-epoxy-4-ethyl-8-methyl-1-(3,4-methylenedioxyphenyl)-3-decene, 4,8-dimetyl-1-(3,4-methylenedioxyphenyl)-2,6-nonadiene and 2,6-dichloro-2,6-dimethyl-9-(3,4-methylenedioxyphenyl)nonane. The results in terms of percent adult emergence are summarized in the following table.

| Compound | Conc., ppm. | Cup 1 | Cup 2 | Cup 3 |
|---|---|---|---|---|
| Nonadiene | 500 | 0 | 0 | 0 |
|  | 100 | 90 | 30 | 10 |
| Decene | 100 | 10 | 20 | 10 |
|  | 10 | 100 | 100 | 100 |
|  | 1 | 100 | 100 | 100 |
|  | 0.1 | 100 | 100 | 100 |
| Nonane | 100 | 0 | 0 | 0 |
|  | 10 | 100 | 90 | 90 |
|  | 1 | 100 | 100 | 100 |
|  | 0.1 | 100 | 100 | 100 |
| Control | — | 100 | 100 | 100 |

The nonadiene gave 100 percent control at 500 ppm. as did the nonane at 100 ppm. The decade gave 80+ percent control at 100 ppm. The control of all the test compounds dropped off at the lower rates.

A number of compounds were tested against housefly larvae by topical application in an acetone solution using the method described above for the primary test against Tenebrio, milkweed bug, wax moth, and Mexican bean bettel. The results of such testing are reported in the following table. The results with the first compound are reported on a scale of 0 to 3 with 0 indicating a normal adult, 1 indicating an adult with deformed wings, 2 indicating a partially emerged adult, and 3 indicating no evidence of emergence. The results for the other compounds are reported onn a scale of 0 to 2 with 0 indicating a normal adult, 1 indicating a partially emerged adult and 2 indicating no evidence of emergence.

| Compound | Conc.,% | Rating 0 | 1 | 2 | 3 |
|---|---|---|---|---|---|
| trans-9-(3,4-dichloro-phenyl)-2,6-dimethyl-2,6-nonadiene | 10 | 5 | — | — | 5 |
|  | 1 | 8 | — | — | 2 |
|  | 0.5 | 3 | — | 1 | 6 |
|  | acet. | 9 | — | — | 1 |
|  | cont. | 8 | — | — | 2 |
| trans-9-(4-chloro-phenyl)-2,6-dimethyl-2,5-nonadiene | 10 | 3 | 1 | 5 |  |
|  | 1 | 3 | 3 | 4 |  |
|  | 0.5 | 4 | — | 6 |  |
|  | acet. | 4 | 1 | 4 |  |
|  | cont. | 6 | 3 | 1 |  |
| cis-9-(4-chlorophenyl)-2,6-dimethyl-2,6-nonadiene | 10 | — | 2 | 6 |  |
|  | 1 | 2 | 2 | 4 |  |
|  | 0.5 | 3 | 3 | 3 |  |
|  | acet. | 4 | — | 5 |  |
|  | cont. | 6 | 1 | 2 |  |
| 2,6-dichloro-2,6-dimethyl-9-(3,4-methylene-dioxyphenyl)nonane | 10 | — | — | 10 |  |
|  | 1 | 1 | — | 9 |  |
|  | 0.5 | 2 | — | 8 |  |
|  | acet. | 10 | — | — |  |
|  | cont. | 9 | — | 1 |  |
| 7,8-epoxy-4-ethyl-8-methyl-1-(3,4-methylenedioxyphenyl)-3-decene | 10 | — | — | 10 |  |
|  | 1 | 5 | 1 | 4 |  |
|  | 0.5 | 6 | — | 4 |  |
|  | acet. | 8 | — | 2 |  |
|  | cont. | 8 | — | 2 |  |
| 2,3-epoxy-2,6-dimethyl-9-(3,4-methylenedioxy-phenyl)-6-nonene | 10 | — | — | 10 |  |
|  | 1 | — | — | 10 |  |
|  | 0.5 | — | — | 10 |  |
|  | acet. | 5 | 1 | 4 |  |
|  | cont. | 9 | 1 | — |  |

Melon Aphids

Young squash plants were dipped for 30 seconds in aqueous solutions containing 200, 100, and 50 ppm. of 2.6-dimethyl-9-(3,4-methylenedioxyphenyl)-2,6-nonadiene. Three plants were treated at each concentration and three plants were used as controls. After the plants had dried, ten adult aphids (*Aphis gossypi*) were placed on each plant and allowed to feed. The plants were maintained under laboratory conditions. Twenty-four hours after they were placed on the plants, all adults were removed, leaving young nymphs. Six days after treatment, the total number of aphids on each plant was determined. The results are summarized in the following table.

| Conc. ppm. | Mature | Immature | Total |
| --- | --- | --- | --- |
| 200 | 2 | 13 | 15 |
| 200 | 9 | 4 | 13 |
| 200 | 1 | 21 | 22 |
| 100 | 0 | 0 | 0 |
| 100 | 12 | 4 | 18 |
| 100 | 4 | 0 | 4 |
| 50 | 5 | 1 | 6 |
| 50 | 7 | 3 | 10 |
| 50 | 12 | 8 | 20 |
| Control | 22 | 9 | 31 |
| Control | 17 | 10 | 27 |
| Control | 26 | 2 | 28 |

In another test, female aphids were placed on young squash plants and allowed to produce young for 24 hours. After 24 hours, all adult aphids were removed from the plants and the young were maintained on the plants for an additional 48-hour period. This gave an aphid nymph population having an age of 48 to 72 hours. To each nymph was applied 0.1 ml. of a 10 percent, 1 percent, or 0.5 percent solution of 2.6-dimethyl-9-(3,4-methylenedioxyphenyl)-2,6-nonadiene or 7,8-epoxy-4-ethyl-8-methyl-1-(3,4-methylenedioxyphenyl)-3-decene in acetone and the aphid nymphs were transferred to new squash plants and observed for possible effects. Ten nymphs were treated with each concentration of each compound and 10 were treated with acetone alone while 10 were not treated to serve as controls. After 3 days, all of the nymphs treated at the 10 percent and 1 percent concentrations were dead while nine of the ten treated with each compound at 0.5 percent concentration were dead. There was only one dead nymph treated with acetone alone and one dead nymph in the nontreated controls.

Alfalfa Weevil

A number of compounds were applied topically to alfalfa weevil larvae as a 10 percent solution in acetone. Acetone and nontreated controls were also run. Ten larvae were used in each test. The number of normal adults emerging from the larvae was observed. In each case, all the acetone and nontreated controls reached normal adulthood. The number of normal adults from treated larvae are reported below.

| Compound | Number of Adults |
| --- | --- |
| 9-(3,4-dimethoxyphenyl)-2,6-dimethyl-2,6-nonadiene | 5 |
| 9-(3,5-dimethoxyphenyl)-2,6-dimethyl-2,6-nonadiene | 8 |
| 9-(3-methoxyphenyl)-2,6-dimethyl-2,6-nonadiene | 6 |
| 9-(3,4-ethylenedioxyphenyl)-2,6-dimethyl-2,6-nonadiene | 7 |

Examples of insects which are members of the orders against which my compounds are active include bean beetle, Tenebrio, confused flour beetle, the corn root worm, potatoe beetle, sawtooth grain beetle, alfalfa weevil, carpet beetle, housefly, yellow-fever mosquito, blow fly, German cockroach, American cockroach, house cricket, grasshopper, milkweed bug, squash bug, kissing bug, assasin bug, bedbug, aphids, leafhoppers, spittle bug, wax moth, Southern army worm, cecropia, tobacco bug worm, and cotton boll worm. Because of the close relationship of insect species within a given order, it is to be expected that all species within the order will exhibit similar behavior toward any particular juvenile hormone or juvenile hormone mimic.

The degree of activity toward a particular insect may vary from compound to compound within my invention. However, it is to be expected that at sufficiently high rates of application all of the compounds will exhibit some activity, although perhaps slight, toward insects belonging to the six orders named above. Simple tests such as those described herein may be used to determine the degree of activity of any particular compound against any particular insect.

Isomerization around the double bonds of my compounds can, and does, occur. Unless a particular isomer is noted, the tests described above were conducted on the mixture of isomers which were obtained in the synthesis of the compound. For example, I have found my products to contain approximately 59 percent of the cis isomer and 41 percent of the trans isomer when prepared by the Wittig reaction. This ratio might be changed by using different conditions such as a different base and a different solvent in the Wittig reaction. It is to be understood that the claims of this application cover all active isomers as well as active mixtures of isomers of compounds of my invention. In those compounds where the pure cis or trans isomer has been obtained, both isomers have been found to exhibit some activity but in general the trans isomers are more active.

The compounds of this invention are active when ingested by the immature insect form or upon contact with the immature insect. This contact may be with the compounds in solid, liquid or vapor states. In general, these compounds are also systemically active, i.e., they may be applied to soil where they will be taken up by the roots of a plant and transported to the foilage which is eaten by the insect form.

The amount of compound needed for field control of insects will depend upon the particular compound being used and the particular insect being treated. In general, the compounds should be applied at a rate of from about 0.2 to about 8 pounds per acre. If more than one insect species is involved, it may be desirable to use a mixture of two or more compounds.

For application, my compounds are incorporated with carriers and adjuvants in accordance with known procedures. They may be formulated, for example, as sprays, dusts, granules, wettable powders or soil drenches. The formulation of such compositions is well known using suitable solids such as silica, fuller's earth, chalk, talc, attapulgite clays, kaolin clays, inorganic carbonates, lime and other known solid carriers. These may be applied as dusts or wettable concentrates may be prepared by including dispersing and emulsifying agents. Liquid concentrates may be obtained using suitable liquid carriers such as xylene, kerosene, aromatic naphthas and other organic solvents. In general, the juvenile hormone mimic is included at a concentration of about 2–50 percent.

When concentrates are prepared for dilution with water they should contain about 1–15 percent of a wetting or emulsifying agent. A large number of such agents are available commercially and are well known to those skilled in the formulation of pesticides. Typical of the surface active agents employed in this manner are the alkyl and alkylaryl polyether alcohols, sulfated higher alcohols and polyester alcohols, alkyl and alkylaryl sulfonates and sulfates, fatty acid amides, polyvinyl alcohols and polyethylene oxides. Other suitable surface active agents are known to those skilled in the art.

It is to be understood that other active ingredients may be included in the formulation and applied with my juvenile hormone mimics. Such other active ingredients include fertilizers, herbicides, fungicides, nematocides, and especially insecticides.

Application of my compounds as a soil drench and foliar spray and the residual fumigant activity of my compounds will be illustrated by the following examples.

EXAMPLE 29

Bean plants of the Bountiful variety were placed in soil and allowed to grow with 10 Mexican bean beetle larvae on each cluster. To the soil around each plant was added 200 ml. of a solution containing 2,6-dimethyl-9-(3,4-methylenedioxyphenyl)-2,6-nonadiene. The soil was then covered with aluminum foil to prevent the larvae from coming in contact with the compound. Three different concentrations of compound were applied. These were prepared from a 48 percent emulsifiable concentrate by diluting 10 ml., 4 ml., and 2 ml. of the concentrate to a volume of 200 ml. with water. A control using 200 ml. of just water and another using no drench were also run. The results are tabulated below using the same rating system as described earlier for the primary screening test agains Mexican bean beetle.

| Conc. | 0 | Rating 1 | 2 | 3 |
|---|---|---|---|---|
| 10 ml. concentrate/200 ml. | 1 | — | — | 9 |
| 4 ml. concentrate/200 ml. | 2 | — | — | 8 |
| 2 ml. concentrate/200 ml. | 8 | — | — | 2 |
| 200 ml. water | 9 | — | — | — |
| No drench | 9 | — | — | — |

EXAMPLE 30

Six-foot by 12-foot caged flats were planted with Bountiful variety bean plants in two 12-foot rows. Into each cage were introduced 100 Mexican bean beetle larvae. Each cage was then sprayed with 500 ml. of a solution prepared by diluting a 48 percent emulsifiable concentrate of 2,6-dimethyl-9-(3,4-methylenedioxyphenyl)-2,6-nonadiene to the desired concentration. Two flats were treated at each concentration and two were used as controls. The results are shown below.

| Rate, lbs./acre | % Control |
|---|---|
| 0.8 | 98.5 |
| 0.4 | 75.5 |
| 0.2 | 71.5 |
| 0.1 | 13 |
| 0 | 4 |

EXAMPLE 31

Fumigant and residual activity of 2,6-dimethyl-9-(3,4-methylenedioxyphenyl)-2,6-nonadiene was determined in the following manner. One milliliter of a 1 percent, a 0.1 percent or a 0.01 percent solution of the test compound was placed in the bottom of a one pint jar. A control was prepared using just acetone. The acetone was allowed to evaporate and 10 Mexican bean beetle larvae were placed on a screen 5 inches from the bottom. The jar was closed for one week at which time the controls emerge as adults and the treated ones are rated as described above. The larvae are replaced weekly. The results of several of the weekly tests are summarized below.

First Week:

| Conc.,% | 0 | Rating 1 | 2 | 3 |
|---|---|---|---|---|
| 1 (10 mg.) | — | — | 1 | 9 |
| 0.1 (1 mg.) | — | — | — | 10 |
| 0.01 (0.1 mg.) | 5 | — | 1 | 4 |
| 0 | 10 | — | — | — |
| Second Week: | | | | |
| 1 | 1 | — | — | 10 |
| 0.1 | — | — | — | 10 |
| 0.01 | 4 | — | 2 | 4 |
| 0 | 9 | — | — | — |
| Fifth Week: | | | | |
| 1 | — | — | — | 10 |
| 0.1 | — | — | — | 10 |
| 0.01 | 10 | — | — | — |
| 0 | 10 | — | — | — |
| Tenth Week: | | | | |
| 1 | — | — | — | 10 |
| 0.1 | 5 | 2 | 1 | 2 |
| 0.01 | 10 | — | — | — |
| 0 | 10 | — | — | — |
| Fifteenth Week | | | | |
| 1 | — | — | — | 10 |
| 0.1 | 10 | — | — | — |
| 0.01 | 10 | — | — | — |
| 0 | 9 | — | — | — |
| Twenty-second Week: | | | | |
| 1 | — | — | — | 10 |
| 0.1 | | Discontinued | | |
| 0.01 | | Discontinued | | |
| 0 | 10 | — | — | — |

Many of my compounds are novel compounds not known before my preparation thereof. The novel compounds of my invention are those having the formula

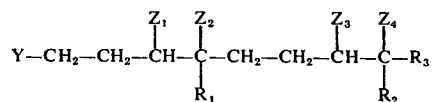

wherein
each of $R_1$, $R_2$ and $R_3$ is a $C_1$–$C_3$ alkyl group;
each of $Z_1$, $Z_2$, $Z_3$ and $Z_4$ separately is hydrogen or halogen, or
$Z_1$ and $Z_2$ together or $Z_3$ and $Z_4$ together are oxygen or a carbon to carbon bond; and
Y is thienyl, phenyl or substituted phenyl wherein the substituents are fluoro, chloro, bromo, carboethoxy, cyano, ethoxy, methylenedioxy, ethylenedioxy, $C_1$–$C_4$ alkyl, nitro, dimethylamino or diethylamino.

Preferred compounds of my invention are those wherein $R_1$, $R_1$ and $R_3$ are methyl or ethyl; $Z_1$ and $Z_2$ together are a carbon to carbon bond; $Z_3$ and $Z_4$ together are oxygen or a carbon to carbon bond; and Y is 3,4-methylenedioxyphenyl or 4-halophenyl, such as 4-chlorophenyl.

I claim:

1. A compound having the formula

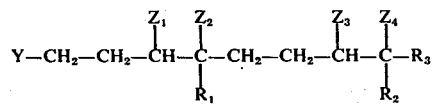

wherein each of $R_1$, $R_2$ and $R_3$ is a $C_1$–$C_3$ alkyl group: [each of $Z_1$, $Z_2$, $Z_3$ and $Z_4$ separately is hydrogen or halogen, or]

$Z_1$ and $Z_2$ together and $Z_3$ and $Z_4$ together are a carbon to carbon bond; and Y is substituted phenyl wherein the substituents are methylenedioxy or ethylenedioxy.

2. The compound of claim 1 wherein each of $R_1$, $R_2$ and $R_3$ is methyl; $Z_1$ and $Z_2$ together and $Z_3$ and $Z_4$ together are carbon to carbon bonds; and Y is 3,4-methylenedioxyphenyl.

3. The compound of claim 1 wherein each of $R_1$ and $R_2$ is methyl; $R_3$ is ethyl; $Z_1$ and $Z_2$ together and $Z_3$ and $Z_4$ together are carbon to carbon bonds; and Y is methylenedioxyphenyl.

* * * * *

UNITED STATES PATENT AND TRADEMARK OFFICE
CERTIFICATE OF CORRECTION

PATENT NO. : 3,962,282
DATED : June 8, 1976
INVENTOR(S) : Thomas L. Emmick

It is certified that error appears in the above-identified patent and that said Letters Patent are hereby corrected as shown below:

Column 10, line 39, "-2,6nonadiene" should read "-2,6-nonadiene".

Column 11, line 53, "-9phenyl-" should read "-9-phenyl-".

Column 11, line 56, "Girgnard" should read "Grignard".

Column 12, line 1, "Y-CHO.HSCH$_2$CH$_2$CH$_2$SH  IsOH" should read "Y-CHO+HSCH$_2$CH$_2$CH$_2$SH  TsOH".

Column 14, line 20, "has" should read "had".

Column 14, line 41, "atomsp-" should read "atmosp-".

Column 16, line 35, after "150°C. and" add "180 microns pressure. The nuclear magnetic resonance spectrum".

Column 17, line 29, "were" should read "where".

Column 22, line 63, "N,N-DIMETYLANILINE" should read "N,N-DIMETHYLANILINE".

Column 23, line 3, "N,N-DIMETYLANILINE" should read "N,N-DIMETHYLANILINE".

Column 26, line 33, "and" should read "are".

Column 26, line 38, "diemthyl" should read "dimethyl".

Column 26, line 68, "25 ppm" should read "2.5 ppm".

Column 28, line 4, "dimetyl" should read "dimethyl".

UNITED STATES PATENT AND TRADEMARK OFFICE
CERTIFICATE OF CORRECTION

PATENT NO. : 3,962,282
DATED : June 8, 1976
INVENTOR(S) : Thomas L. Emmick

It is certified that error appears in the above-identified patent and that said Letters Patent are hereby corrected as shown below:

Column 28, line 24, "decade" should read "decene".

Column 28, line 32, "bettel" should read "beetle".

Column 28, line 38, "onn" should read "on".

Column 29, line 5, "2.6-" should read "2,6-".

Column 29, line 37, "2.6-" should read "2,6-".

Column 30, line 2, Add complete paragraph immediately following table. "The activity of my compounds has been demonstrated against a number of orders of insects including Coleoptera, Diptera, Orthoptera, Hemiptera, Homoptera, and Lepidoptera.".

Column 31, line 17, "polyester" should read "polyether".

Column 31, line 47, "agains" should read "against".

Column 33, line 5, "$R_1$, $R_1$ and $R_3$" should read "$R_1$, $R_2$ and $R_3$"

Column 34, line 5, "Zand" should read "$Z_1$ and".

Signed and Sealed this

Fourteenth Day of December 1976

[SEAL]

Attest:

RUTH C. MASON
Attesting Officer

C. MARSHALL DANN
Commissioner of Patents and Trademarks